(12) United States Patent
Sung et al.

(10) Patent No.: US 7,879,361 B2
(45) Date of Patent: *Feb. 1, 2011

(54) NANOPARTICLES FOR DRUG DELIVERY

(75) Inventors: Hsing-Wen Sung, Hsinchu (TW);
Yu-Hsin Lin, Kaohsiung (TW);
Mei-Chin Chen, Taipei County (TW);
Hosheng Tu, Newport Beach, CA (US)

(73) Assignees: GP Medical, Inc., Newport Beach, CA (US); National Tsing Hua University, Hsinchu (TW)

( * ) Notice: Subject to any disclaimer, the term of this patent is extended or adjusted under 35 U.S.C. 154(b) by 1251 days.

This patent is subject to a terminal disclaimer.

(21) Appl. No.: 11/442,192

(22) Filed: May 26, 2006

(65) Prior Publication Data

US 2007/0237827 A1 Oct. 11, 2007

Related U.S. Application Data

(63) Continuation-in-part of application No. 11/398,440, filed on Apr. 5, 2006, now Pat. No. 7,291,598, which is a continuation-in-part of application No. 11/284,734, filed on Nov. 21, 2005, now Pat. No. 7,282,194, which is a continuation-in-part of application No. 11/029,082, filed on Jan. 4, 2005, now Pat. No. 7,265,090.

(51) Int. Cl.
*A61K 9/14* (2006.01)
*A61K 9/50* (2006.01)

(52) U.S. Cl. .............. 424/491; 424/408; 424/451; 424/452; 424/463; 424/500

(58) Field of Classification Search ............. 424/451, 424/452, 456, 489, 455, 491, 500
See application file for complete search history.

(56) References Cited

U.S. PATENT DOCUMENTS

| 6,383,478 | B1 * | 5/2002 | Prokop et al. ............ 424/78.08 |
|---|---|---|---|
| 6,777,552 | B2 | 8/2004 | Niddam-Hildesheim et al. |
| 7,265,090 | B2 * | 9/2007 | Sung et al. .................. 514/12 |
| 7,282,194 | B2 * | 10/2007 | Sung et al. ................ 424/1.69 |
| 7,455,830 | B2 * | 11/2008 | Sung et al. ................ 424/1.69 |
| 7,541,028 | B2 * | 6/2009 | Sung et al. ............... 424/130.1 |
| 7,541,046 | B1 * | 6/2009 | Sung et al. .................. 424/408 |
| 2004/0219208 | A1 * | 11/2004 | Kawamura et al. .......... 424/468 |
| 2004/0225077 | A1 * | 11/2004 | Gravett et al. ............... 525/418 |
| 2005/0042298 | A1 | 2/2005 | Pardridge et al. |
| 2006/0051424 | A1 | 3/2006 | Leong et al. |

OTHER PUBLICATIONS

Lin Yh et al., "Preparation of nanoparticles composed of chitosan/poly-r-glutamic acid and evaluation of their permeability through Caco-2 cells", 2005.
Biomacromolecules 2005;6:1104-1112.
O'Riordan Michael "High-dose atorvastatin reduces ventricular arrhythmias in CAD patients with an ICD" HRS news, May 22, 2006.
Hughes Sue "Statins could be gastroprotective" the Heart.org, May 8, 2006.
Adis International Ltd. "ALX 111:Alx1-11, parathroid hormone (1-84) -NPS Allelix, Preos, PTH, recombinant human parathyroid hormone, rhPTH (1-84)" Drugs R D. 2003;4(4):231-235.

* cited by examiner

*Primary Examiner*—Michael G Hartley
*Assistant Examiner*—Micah-Paul Young

(57) ABSTRACT

The invention discloses the nanoparticles composed of chitosan, poly-glutamic acid, and at least one bioactive agent of HMG-CoA reductase inhibitors or erythropoietin. The nanoparticles are characterized with a positive surface charge and their enhanced permeability for paracellular drug delivery.

16 Claims, 16 Drawing Sheets

Figure 2
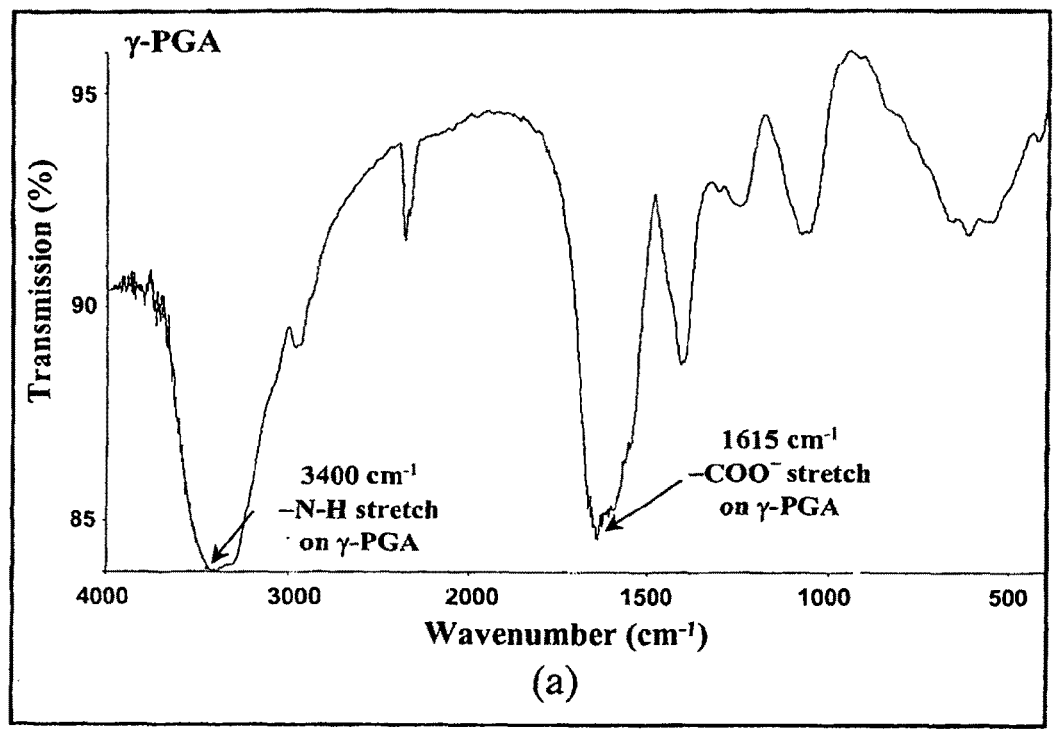
(a)
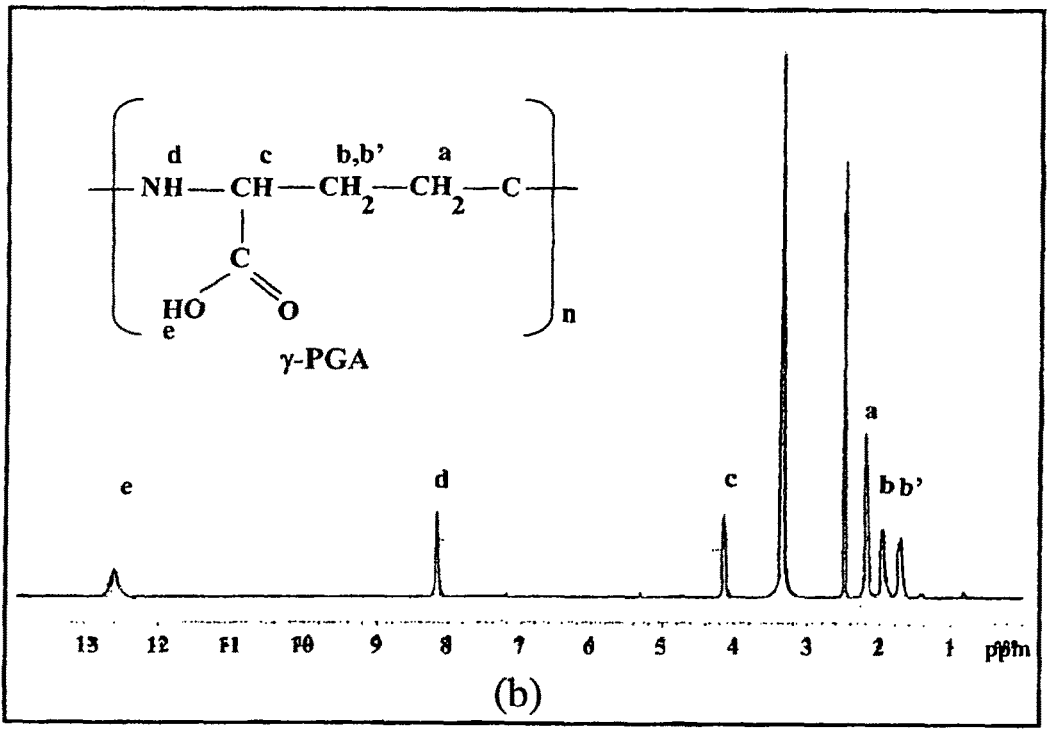
(b)

NANOPARTICLES FOR DRUG DELIVERY

CROSS-REFERENCE TO RELATED APPLICATIONS

This application is a continuation-in-part application of U.S. patent application Ser. No. 11/398,440, filed Apr. 5, 2006, now U.S. Pat. No. 7,291,598 B2, issued Nov. 6, 2007, which is a continuation-in-part application of U.S. patent application Ser. No. 11/284,734, filed Nov. 21, 2005, now U.S. Pat. No. 7,282,194 B2, issued Oct. 16, 2007, which is a continuation-in-part application of U.S. patent application Ser. No. 11/029,082, filed Jan. 4, 2005, now U.S. Pat. No. 7,265,090 B2, issued Sep. 4, 2007, the entire contents of which are incorporated herein by reference.

FIELD OF THE INVENTION

The present invention is related to formulation and medical uses of biodegradable nanoparticles with therapeutic bioactive agents and their oral delivery having enhanced paracellular permeability.

BACKGROUND OF THE INVENTION

Production of pharmaceutically active peptides and proteins in large quantities has become feasible (Biomacromolecules 2004;5:1917-1925). The oral route is considered the most convenient way of drug administrations for patients. Nevertheless, the intestinal epithelium is a major barrier to the absorption of hydrophilic drugs such as peptides and proteins (J. Control. Release 1996;39:131-138). This is because hydrophilic drugs cannot easily diffuse across the cells through the lipid-bilayer cell membranes. Attentions have been given to improving paracellular transport of hydrophilic drugs (J. Control. Release 1998;51:35-46). The transport of hydrophilic molecules via the paracellular pathway is, however, severely restricted by the presence of tight junctions that are located at the luminal aspect of adjacent epithelial cells (Annu. Rev. Nutr. 1995;15:35-55). These tight junctions form a barrier that limits the paracellular diffusion of hydrophilic molecules. The structure and function of tight junctions is described, inter alia, in Ann. Rev. Physiol. 1998;60:121-160 and in Ballard T S et al., Annu. Rev. Nutr. 1995;15:35-55. Tight junctions do not form a rigid barrier but play an important role in the diffusion through the intestinal epithelium from lumen to bloodstream and vice versa.

Movement of solutes between cells, through the tight junctions that bind cells together into a layer as with the epithelial cells of the gastrointestinal tract, is termed paracellular transport. Paracellular transport is passive. Paracellular transport depends on electrochemical gradients generated by transcellular transport and on solvent drag through tight junctions. Tight junctions form an intercellular barrier that separates the apical and basolateral fluid compartments of a cell layer. Movement of a solute through a tight junction from apical to basolateral compartments depends on the "tightness" of the tight junction for that solute.

Polymeric nanoparticles have been widely investigated as carriers for drug delivery (Biomaterials 2002;23:3193-3201). Much attention has been given to the nanoparticles made of synthetic biodegradable polymers such as poly-ε-caprolactone and polylactide due to their good biocompatibility (J. Drug Delivery 2000;7:215-232; Eur. J. Pharm. Biopharm. 1995;41:19-25). However, these nanoparticles are not ideal carriers for hydrophilic drugs because of their hydrophobic property. Some aspects of the invention relate to a novel nanoparticle system, composed of hydrophilic chitosan and poly(glutamic acid) hydrogels that is prepared by a simple ionic-gelation method. This technique is promising as the nanoparticles are prepared under mild conditions without using harmful solvents. It is known that organic solvents may cause degradation of peptide or protein drugs that are unstable and sensitive to their environments (J. Control. Release 2001; 73:279-291).

Following the oral drug delivery route, protein drugs are readily degraded by the low pH of gastric medium in the stomach. The absorption of protein drugs following oral administration is challenging due to their high molecular weight, hydrophilicity, and susceptibility to enzymatic inactivation. Protein drugs at the intestinal epithelium could not partition into the hydrophobic membrane and thus can only traverse the epithelial barrier via the paracellular pathway. However, the tight junction forms a barrier that limits the paracellular diffusion of hydrophilic molecules.

Chitosan (CS), a cationic polysaccharide, is generally derived from chitin by alkaline deacetylation (J. Control. Release 2004;96:285-300). It was reported from literature that CS is non-toxic and soft-tissue compatible (Biomacromolecules 2004;5:1917-1925; Biomacromolecules 2004;5: 828-833). Additionally, it is known that CS has a special feature of adhering to the mucosal surface and transiently opening the tight junctions between epithelial cells (Pharm. Res. 1994;11:1358-1361). Most commercially available CSs have a quite large molecular weight (MW) and need to be dissolved in an acetic acid solution at a pH value of approximately 4.0 or lower that is sometimes impractical. However, there are potential applications of CS in which a low MW would be essential. Given a low MW, the polycationic characteristic of CS can be used together with a good solubility at a pH value close to physiological ranges (Eur. J. Pharm. Biopharm. 2004;57:101-105). Loading of peptide or protein drugs at physiological pH ranges would preserve their bioactivity. On this basis, a low-MW CS, obtained by depolymerizing a commercially available CS using cellulase, is disclosed herein to prepare nanoparticles of the present invention.

The γ-PGA, an anionic peptide, is a natural compound produced as capsular substance or as slime by members of the genus *Bacillus* (Crit. Rev. Biotechnol. 2001;21:219-232). γ-PGA is unique in that it is composed of naturally occurring L-glutamic acid linked together through amide bonds. It was reported from literature that this naturally occurring γ-PGA is a water-soluble, biodegradable, and non-toxic polymer. A related, but structurally different polymer, [poly(α-glutamic acid), α-PGA] has been used for drug delivery (Adv. Drug Deliver. Rev. 2002;54:695-713; Cancer Res. 1998;58:2404-2409). α-PGA is usually synthesized from poly(γ-benzyl-L-glutamate) by removing the benzyl protecting group with the use of hydrogen bromide. Hashida et al. used α-PGA as a polymeric backbone and galactose moiety as a ligand to target hepatocytes (J. Control. Release 1999;62:253-262). Their in vivo results indicated that the galactosylated α-PGA had a remarkable targeting ability to hepatocytes and degradation of α-PGA was observed in the liver.

Thanou et al. reported chitosan and its derivatives as intestinal absorption enhancers (Adv Drug Deliv Rev 2001;50: S91-S101). Chitosan, when protonated at an acidic pH, is able to increase the paracellular permeability of peptide drugs across mucosal epithelia. Co-administration of chitosan or trimethyl chitosan chloride with peptide drugs were found to substantially increase the bioavailability of the peptide in animals compared with administrations without the chitosan component.

U.S. Patent Application publication no. 2006/0051424A1, published on Mar. 9, 2006, entire contents of which are incorporated herein by reference, discloses nanoparticle compositions comprising a cationic biopolymer and at least one biologically active substance, pharmaceutical compositions comprising such nanoparticles and methods for the oral administration of biologically active molecules which are susceptible to degradation in the gastro-intestinal tract using nanoparticle.

U.S. Patent Application publication no. 2005/0042298A1, published on Feb. 24, 2005, entire contents of which are incorporated herein by reference, discloses a functionalized composition for use in forming an immunonanoparticle, the functionalized composition comprising a nanoparticle-forming polymer, a polymeric strand having a first end attached to the nanoparticle-forming polymer and a second end, and a conjugation agent attached to the second end of the polymeric strand. In one embodiment, a functionalized moiety for use in forming the immunonanoparticle further includes a targeting agent attached to the conjugation agent.

U.S. Pat. No. 6,689,338 B2 issued on Feb. 10, 2004, entire contents of which are incorporated herein by reference, discloses a bioconjugate comprising a radioactive, metal sulfide or metal oxide nanoparticle covalently linked to at least one biological vector molecule, wherein the at least one biological vector molecule is selected from a group consisting of monoclonal antibodies (mAb), fragments of monoclonal antibodies, and peptides.

U.S. Pat. No. 6,165,440, issued on Dec. 26, 2000, entire contents of which are incorporated herein by reference, discloses a method of anti-cancer drug delivery in a solid tumor, comprising the steps of administering at least one anti-cancer drug to the tumor, injecting nanoparticles or microparticles to the tumor intravenously, and irradiating the tumor with radiation, wherein the anti-cancer drug is selected from the group consisting of a monoclonal antibody, a cytokine, an antisense oligonucleotide, and a gene-targeting vector.

U.S. Pat. No. 6,777,552, issued on Aug. 17, 2004, entire contents of which are incorporated herein by reference, discloses processes for preparing a calcium salt of a statin from an ester derivative or protected ester derivative of the statin by using calcium hydroxide.

Currently, most statin is administered to a patient orally on a daily basis. It is desirable to administer statin or other therapeutic drugs orally in a nanoparticle form that provide enhanced paracellular permeability, bioavailability, and sustained release over an extended period, where the nanoparticles biodegrade to biocompatible byproducts in situ.

SUMMARY OF THE INVENTION

It is one object of the present invention to provide a novel nanoparticle system and methods of preparation for paracellular transport drug delivery using a simple and mild ionic-gelation method upon addition of a poly-γ-glutamic acid (γ-PGA) solution into a low molecular weight chitosan (low-MW CS) solution. In one embodiment, the molecular weight of a low-MW CS of the present invention is about 80 kDa or less, preferably at about 40 kDa, adapted for adequate solubility at a pH that maintains the bioactivity of protein and peptide drugs. It is stipulated that a chitosan particle with about 30-50 kDa molecular weight is kidney inert. The particle size and the zeta potential value of the prepared nanoparticles are controlled by their constituted compositions.

The results obtained by the TEM (transmission electron microscopy) and AFM (atomic force microscopy) examinations showed that the morphology of the prepared nanoparticles was generally spherical in shape. Evaluation of the prepared nanoparticles in enhancing intestinal paracellular transport was investigated in vitro in Caco-2 cell monolayers. In some aspects of the present invention, it provides the nanoparticles with CS dominated on the surfaces to effectively reduce the transepithelial electrical resistance (TEER) of Caco-2 cell monolayers. The confocal laser scanning microscopy (CLSM) observations confirm that the nanoparticles with CS dominated on the surface are able to open the tight junctions between Caco-2 cells and allows transport of the nanoparticles via the paracellular pathways.

In some application, a normal or high molecular weight chitosan is used in preparing the nanoparticles.

Some aspects of the invention relate to a method of enhancing intestinal or blood brain paracellular transport configured for delivering at least one bioactive agent in a patient comprising administering nanoparticles composed of γ-PGA and chitosan, wherein the step of administering the nanoparticles may be via oral administration. In one embodiment, the chitosan dominates on a surface of the nanoparticles as shell substrate and the negatively charged γ-PGA as core substrate. In another embodiment, a substantial surface of the nanoparticles is characterized with a positive surface charge. In a further embodiment, the nanoparticles of the present invention comprise at least one positively charged shell substrate and at least one negatively charged core substrate. In one embodiment, at least one bioactive or protein drug is conjugated with the negatively charged core substrate.

In a further embodiment, the chitosan of the nanoparticles is a low molecular weight chitosan, wherein the low molecular weight chitosan has a molecular weight of about 50 kDa, preferably having a molecular weight of less than about 40 kDa.

In a further embodiment, the nanoparticles have a mean particle size between about 50 and 400 nanometers, preferably between about 100 and 300 nanometers, and most preferably between about 100 and 200 nanometers.

In some embodiments, the nanoparticles are loaded with a therapeutically effective amount of at least one bioactive agent, wherein the bioactive agent is selected from a group consisting of synthetic drugs, proteins (for example, monoclonal antibodies), peptides, nucleosides, nucleotides, antiviral agents, antineoplastic agents, antibiotics, and anti-inflammatory drugs. Further, the bioactive agent may be selected from a group consisting of calcitonin, cyclosporin, insulin, oxytocin, tyrosine, enkephalin, tyrotropin releasing hormone, follicle stimulating hormone, luteinizing hormone, vasopressin and vasopressin analogs, catalase, superoxide dismutase, interleukin-II, interferon, colony stimulating factor, tumor necrosis factor (TNF) and melanocyte-stimulating hormone. In one preferred embodiment, the bioactive agent is an Alzheimer antagonist.

Some aspects of the invention relate to an oral dose of nanoparticles that effectively enhance intestinal or blood brain paracellular transport comprising γ-PGA or α-PGA and low molecular weight chitosan, wherein the chitosan dominates on a surface of the nanoparticles. Some aspects of the invention relate to an oral dose of nanoparticles that effectively enhance intestinal or blood brain paracellular transport comprising a negative component, such as γ-PGA, α-PGA, heparin, or heparan sulfate, in the core and low molecular weight chitosan, wherein the chitosan dominates on a surface of the nanoparticles with positive charges. In a further embodiment, the nanoparticles comprise at least one bioactive agent, such as insulin, insulin analog, Alzheimer's disease antagonist, Parkison's disease antagonist, or other protein/peptide. The bioactive agent for treating Alzheimer's disease may include memantine hydrochloride (Axura® by Merz Pharmaceuticals), donepezil hydrochloride (Aricept® by Eisai Co. Ltd.), rivastigmine tartrate (Exelong by Novartis), galantamine hydrochloride (Reminyl®) by Johnson & Johnson), and tacrine hydrochloride (Cognex® by Parke Davis). Examples of insulin or insulin analog products include, but not limited to, Humulin® (by Eli Lilly), Humalog® (by Eli Lilly) and Lantus® (by Aventis).

Some aspects of the invention relate to an oral dose of nanoparticles that effectively enhance intestinal or blood brain paracellular transport comprising γ-PGA and low molecular weight chitosan, wherein the nanoparticles are crosslinked with a crosslinking agent or with light, such as ultraviolet irradiation.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle. In one embodiment, the third component is γ-PGA, α-PGA, derivatives or salts of PGA, heparin, glycosaminoglycans or alginate. In another embodiment, the first component comprises insulin at a concentration range of 0.075 to 0.091 mg/ml, the second component at a concentration range of 0.67 to 0.83 mg/ml, and the third component comprises γ-PGA at a concentration range of 0.150 to 0.184 mg/ml.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle, wherein the at least one bioactive agent is an antagonist for Alzheimer's disease or is for treating Alzheimer's disease selected from the group consisting of memantine hydrochloride, donepezil hydrochloride, rivastigmine tartrate, galantamine hydrochloride, and tacrine hydrochloride. In a further embodiment, the at least one bioactive agent is insulin or insulin analog. In still another embodiment, the at least one bioactive agent is selected from the group consisting of proteins, peptides, nucleosides, nucleotides, antiviral agents, antineoplastic agents, antibiotics, and anti-inflammatory drugs.

Some aspects of the invention provide a dose of nanoparticles characterized by enhancing intestinal or brain blood paracellular transport, wherein the nanoparticles are further encapsulated in a gelcap.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle, wherein the second component is crosslinked. In one embodiment, the degree of crosslinking is less than 50%. In another embodiment, the degree of crosslinking is ranged between 1% and 20%.

Some aspects of the invention provide a dose of nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the nanoparticle, wherein the second component is crosslinked with a crosslinking agent selected from the group consisting of genipin, its derivatives, analog, stereoisomers and mixtures thereof. In one embodiment, the crosslinking agent is selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl) phosphine, ascorbate-copper, glucose-lysine and photo-oxidizers.

Some aspects of the invention provide a dose of nanoparticles characterized by enhancing intestinal or brain blood paracellular transport, wherein the low molecule weight chitosan has a molecular weight of 80 kDa or less. In one embodiment, the low molecule weight chitosan is further grafted with a polymer having a chemical formula as:

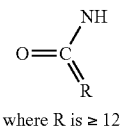

where R is ≥ 12

Some aspects of the invention provide a method of enhancing intestinal or brain blood paracellular transport comprising administering a dose of nanoparticles, wherein each nanoparticle comprises a first component of at least one bioactive agent, a second component of low molecular weight chitosan, and a third component that is negatively charged, wherein the second component dominates on a surface of the nanoparticle. In one embodiment, the step of administering the dose of nanoparticles is via oral administration for enhancing intestinal paracellular transport. In another embodiment, the step of administering the dose of nanoparticles is via venous administration or injection for enhancing brain blood paracellular transport or reducing the blood-brain barrier (BBB).

Some aspects of the invention provide a method of treating diabetes of a patient comprising orally administering insulin containing nanoparticles with a dosage effective amount of the insulin to treat the diabetes, wherein at least a portion of the nanoparticles comprises a positively charged shell substrate and a negatively charged core substrate. In one embodiment, the shell substrate comprises chitosan, chitin, chitosan oligosaccharides, and chitosan derivatives thereof, wherein a substantial portion of a surface of the nanoparticles is characterized with a positive surface charge. In another embodiment, the core substrate is selected from a group consisting of γ-PGA, α-PGA, water-soluble salts of PGA, metal salts of PGA, heparin, heparin analogs, low molecular weight heparin, glycosaminoglycans, and alginate. The molecular formula of the insulin is selected from a group consisting of $C_{254}H_{377}N_{65}O_{75}S_6$, $C_{257}H_{383}N_{65}O_{77}S_6$, $C_{256}H_{381}N_{65}O_{79}S_6$, $C_{267}H_{404}N_{72}O_{78}S_6$, and the like.

In one embodiment, the orally administering insulin containing nanoparticles comprise a dosage effective amount of the insulin to treat the diabetes comprising an insulin amount of between about 15 units to 45 units, preferably between about 25 units to 35 units, per kilogram body weight of the patient. In a further embodiment, the insulin-containing nanoparticle comprises a trace amount of zinc or calcium, or is treated with enteric coating.

In one embodiment, the insulin containing nanoparticles further comprise at least one paracellular transport enhancer, wherein the paracellular transport enhancer may be selected from a group consisting of $Ca^{2+}$ chelators, bile salts, anionic surfactants, medium-chain fatty acids, and phosphate esters. In another embodiment, the nanoparticles and the paracellular transport enhancer are co-encapsulated in a softgel capsule or are encapsulated separately.

Some aspects of the invention provide nanoparticles for oral administration in a patient, comprising a positively charged shell substrate, a negatively charged core substrate, and a bioactive agent conjugated with the core substrate, wherein the core substrate is selected from a group consisting of heparin, heparin analogs, low molecular weight heparin, glycosaminoglycans, and alginate, the bioactive agent being selected from a group consisting of chondroitin sulfate, hyaluronic acid, growth factor and protein with pharmaceutically effective amount.

Some aspects of the invention provide nanoparticles for oral administration in a patient, comprising a positively charged shell substrate, a negatively charged core substrate, and a bioactive agent conjugated with the core substrate, wherein the bioactive agent is calcitonin or vancomycin.

Some aspects of the invention provide a method of treating Alzheimer's diseases of a patient comprising intravenously administering bioactive nanoparticles with a dosage effective to treat the Alzheimer's diseases, wherein the bioactive nanoparticles comprises a positively charged shell substrate, a negatively charged core substrate, and at least one bioactive agent for treating Alzheimer's disease, wherein the at least one bioactive agent is selected from a group consisting of memantine hydrochloride, donepezil hydrochloride, rivastigmine tartrate, galantamine hydrochloride, and tacrine hydrochloride.

In one embodiment, the dosage effective to treat the Alzheimer's diseases comprises administering the at least one bioactive agent for treating Alzheimer's disease at about 10 mg to 40 mg per day over a period of one month to one year. In another embodiment, at least a portion the shell substrate is crosslinked, preferably at a degree of crosslinking less than about 50%, or most preferably between about 1% and 20%.

Some aspects of the invention provide a method of treating a target tissue or organ of a patient with a monoclonal antibody, comprising the steps of: providing the monoclonal antibody to the tissue or organ, wherein the monoclonal antibody is encapsulated within nanoparticles; administering the nanoparticles to the patient orally; and treating the target tissue or organ with the monoclonal antibody that is sustained released from the nanoparticles. In one embodiment, the monoclonal antibody is an anti-cancer drug. In another embodiment, the monoclonal antibody is Adalimumab or Bevacizumab.

Some aspects of the invention provide nanoparticles for oral administration in a patient, comprising a positively charged shell substrate, a negatively charged core substrate, and a monoclonal antibody encapsulated within the shell substrate. In one preferred embodiment, the monoclonal antibody is mixed with, conjugated or coupled to, the core substrate.

Some aspects of the invention provide a method of delivering an HMG-CoA reductase inhibitor to blood circulation in a patient, comprising: (a) providing nanoparticles that encapsulate the HMG-CoA reductase inhibitor, wherein the nanoparticles are biodegradable; (b) administering the nanoparticles orally that move toward an intestine of the patient; (c) urging the nanoparticles to pass through an epithelial barrier of the intestine; and (d) releasing the HMG-CoA reductase inhibitor into the blood circulation through the capillaries surrounding the exterior surface of the intestine in a sustained manner.

Some aspects of the invention provide a pharmaceutical composition of nanoparticles for oral administration in a patient, comprising a biodegradable chitosan shell substrate, and a HMG-CoA reductase inhibitor encapsulated within the shell substrate, wherein the released HMG-CoA reductase inhibitor is pharmaceutically effective. In one embodiment, the HMG-CoA reductase inhibitor is released into blood circulation in a sustained manner. In another embodiment, the HMG-CoA reductase inhibitor is released via diffusion, biodegradation of the shell substrate, or both.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

FIG. 2 shows (a) FT-IR and (b) $^1$H-NMR spectra of the purified γ-PGA obtained from microbial fermentation.

DETAILED DESCRIPTION OF THE EXEMPLARY EMBODIMENTS

Figure 1:
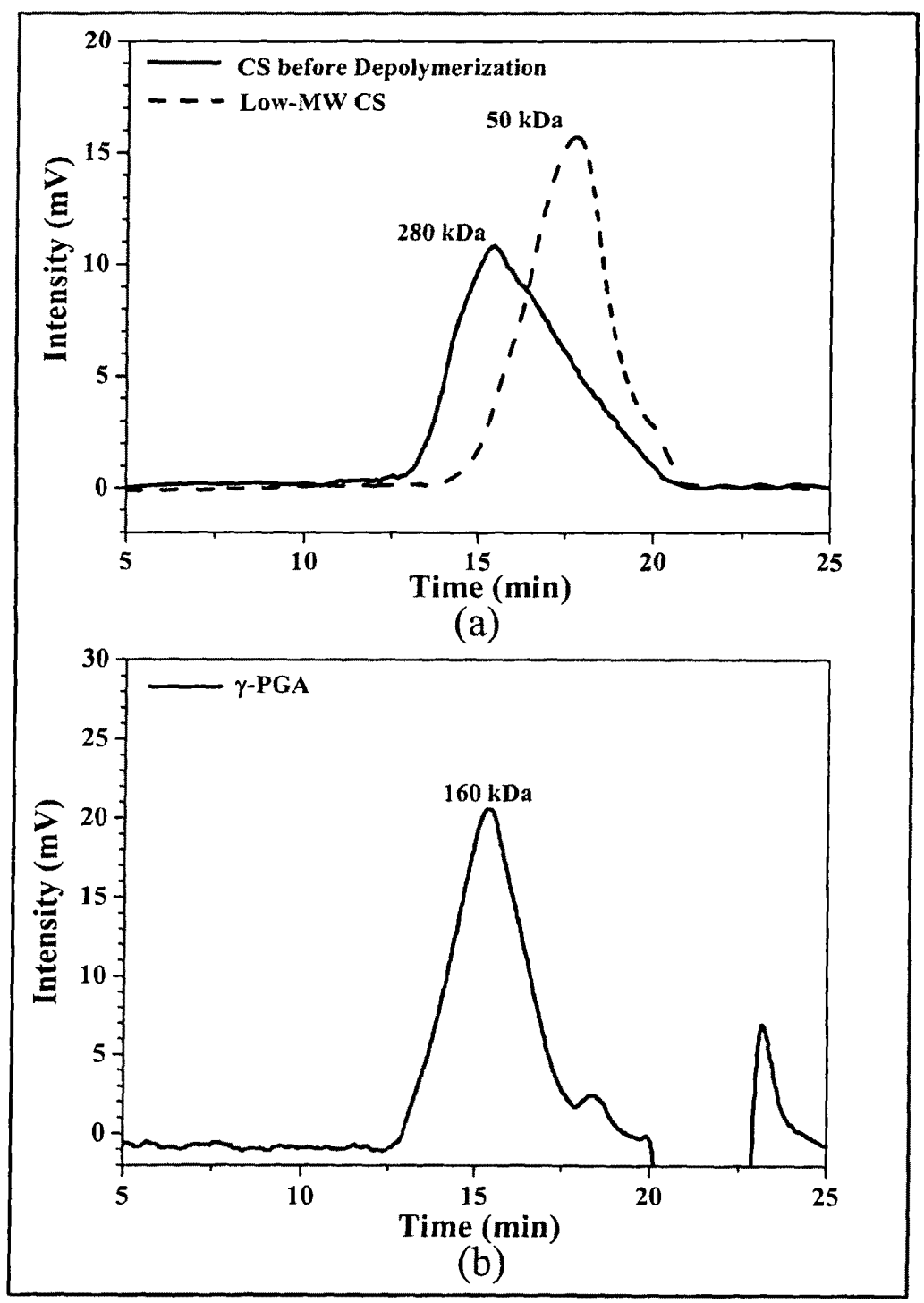
FIG. 1 shows GPC chromatograms of (a) standard-MW CS before depolymerization and the low-MW CS after depolymerization; (b) the purified γ-PGA obtained from microbial fermentation.

The preferred embodiments of the present invention described below relate particularly to preparation of nanoparticles composed of chitosan/poly-glutamic acid/insulin and their permeability to enhance the intestinal or blood brain paracellular permeation by opening the tight junctions between epithelial cells. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

γ-PGA is a naturally occurring anionic homo-polyamide that is made of L-glutamic acid units connected by amide linkages between α-amino and γ-carboxylic acid groups (Crit. Rev. Biotechnol. 2001;21:219-232). It is an exocellular polymer of certain *Bacillus* species that is produced within cells via the TCA cycle and is freely excreted into the fermentation broth. Its exact biological role is not fully known, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

EXAMPLE NO. 1

Materials and Methods of Nanoparticles Preparation

CS (MW ~$2.8 \times 10^5$) with a degree of deacetylation of approximately 85% was acquired from Challenge Bioproducts Co. (Taichung, Taiwan). Acetic acid, cellulase (1.92 units/mg), fluorescein isothiocyanate (FITC), phosphate buffered saline (PBS), periodic acid, sodium acetate, formaldehyde, bismuth subnitrate, and Hanks balanced salt solution (HBSS) were purchased from Sigma Chemical Co. (St. Louis, Mo.). Ethanol absolute anhydrous and potassium sodium tartrate were obtained from Merck (Darmstadt, Germany). Non-essential amino acid (NEAA) solution, fetal bovine serum (FBS), gentamicin and trypsin-EDTA were acquired from Gibco (Grand Island, N.Y.). Eagle's minimal essential medium (MEM) was purchased from Bio West (Nuaille, France). All other chemicals and reagents used were of analytical grade.

EXAMPLE NO. 2

Depolymerization of CS by Enzymatic Hydrolysis

Regular CS was treated with enzyme (cellulase) to produce low-MW CS according to a method described by Qin et al. with some modifications (Food Chem. 2004;84:107-115). A solution of CS (20 g/l) was prepared by dissolving CS in 2% acetic acid. Care was taken to ensure total solubility of CS. Then, the CS solution was introduced into a vessel and adjusted to the desired pH 5.0 with 2N aqueous NaOH. Subsequently, cellulase (0.1 g) was added into the CS solution (100 ml) and continuously stirred at 37° C. for 12 hours. Afterward, the depolymerized CS was precipitated with aqueous NaOH at pH 7.0-7.2 and the precipitated CS was washed three times with deionized water. The resulting low-MW CS was lyophilized in a freeze dryer (Eyela Co. Ltd, Tokyo, Japan).

The average molecular weight of the depolymerized CS was determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000-F, SFD, Torrance, Calif.). Polysaccharide standards (molecular weights range from 180 to 788,000, Polymer Laboratories, UK) were used to construct a calibration curve. The mobile phase contained $0.01M NaH_2PO_4$ and $0.5M NaNO_3$ and was brought to a pH of 2.0. The flow rate of mobile phase was 1.0 ml/min, and the columns and the RI detector cell were maintained at 30° C.

Factors limiting applications of most commercially available CSs are their high molecular weight and thus high viscosity and poor solubility at physiological pH ranges. Low-MW CS overcomes these limitations and hence finds much wider applications in diversified fields. It was suggested that low-MW CS be used as a parenteral drug carrier due to its lower antigen effect (Eur. J. Pharm. Biopharm. 2004;57:101-105). Low-MW CS was used as a non-viral gene delivery system and showed promising results (Int. J. Pharm. 1999; 178:231-243). Other studies based on animal testing showed the possibilities of low-MW CS for treatment of type 2 diabetes and gastric ulcer (Biol. Pharm. Bull. 2002;25:188-192). Several hydrolytic enzymes such as lysozyme, pectinase, cellulase, bromelain, hemicellulase, lipase, papain and the like can be used to depolymerize CS (Biochim. Biophys. Acta 1996;1291:5-15; Biochem. Eng. J. 2001;7:85-88; Carbohydr. Res. 1992;237:325-332). FIG. 1*a* shows GPC chromatograms of both standard-MW (also known as regular-MW) and low-MW CS. It is known that cellulase catalyzes the cleavage of the glycosidic linkage in CS (Food Chem. 2004; 84:107-115). The low-MW CS used in the study was obtained by precipitating the depolymerized CS solution with aqueous NaOH at pH 7.0-7.2. Thus obtained low-MW CS had a MW of about 50 kDa (Figure 1*a*). In a preferred embodiment, the low molecular weight chitosan has a molecular weight of less than about 40 kDa, but above 10 kDa. Other forms of chitosan may also be applicable, including chitin, chitosan oligosaccharides, and derivatives thereof.

It was observed that the obtained low-MW CS can be readily dissolved in an aqueous solution at pH 6.0, while that before depolymerization needs to be dissolved in an acetic acid solution with a pH value about 4.0. Additionally, it was found that with the low-MW CS, the prepared nanoparticles had a significantly smaller size with a narrower distribution than their counterparts prepared with the high-MW (also known as standard-MW) CS (before depolymerization), due to its lower viscosity. As an example, upon adding a 0.10% γ-PGA aqueous solution into a 0.20% high-MW CS solution (viscosity 5.73±0.08 cp, measured by a viscometer), the mean particle size of the prepared nanoparticles was 878.3±28.4 nm with a polydispersity index of 1.0, whereas adding a 0.10% γ-PGA aqueous solution into the low-MW CS solution (viscosity 1.29±0.02 cp) formed nanoparticles with a mean particle size of 218.1±4.1 nm with a polydispersity index of 0.3 (n=5).

EXAMPLE NO. 3

Production and Purification of γ-PGA

γ-PGA was produced by *Bacillus licheniformis* (ATCC 9945, Bioresources Collection and Research Center, Hsinchu, Taiwan) as per a method reported by Yoon et al. with slight modifications (Biotechnol. Lett. 2000;22:585-588). Highly mucoid colonies (ATCC 9945a) were selected from *Bacillus licheniformis* (ATCC 9945) cultured on the E medium (ingredients comprising L-glutamic acid, 20.0 g/l; citric acid, 12.0 g/l; glycerol, 80.0 g/l; $NH_4Cl$, 7.0 g/l; $K_2HPO_4$, 0.5 g/l; $MgSO_4.7H_2O$, 0.5 g/l; $FeCl_3.6H_2O$, 0.04 g/l; $CaCl_2.2H_2O$, 0.15 g/l; $MnSO_4.H_2O$, 0.104 g/l, pH 6.5) agar plates at 37° C. for several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-l jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and/or 2M HCl. The dissolved oxygen concentration was initially controlled at 40% of air saturation by supplying air and by controlling the agitation speed up to 1000 rpm.

After 40 hours, cells were separated from the culture broth by centrifugation for 20 minutes at 12,000× g at 4° C. The supernatant containing γ-PGA was poured into 4 volumes of methanol and left overnight with gentle stirring. The resulting precipitate containing crude γ-PGA was collected by centrifugation for 40 minutes at 12,000× g at 4° C. and then was dissolved in deionized water to remove insoluble impurities by centrifugation for 20 minutes at 24,000× g at 4° C. The aqueous γ-PGA solution was desalted by dialysis (MWCO: 100,000, Spectrum Laboratories, Inc., Laguna Hills, Calif.) against distilled water for 12 hours with water exchanges several times, and finally was lyophilized to obtain pure γ-PGA.

The purified γ-PGA was verified by the proton nuclear magnetic resonance ($^1$H-NMR) and the FT-IR analyses. Analysis of $^1$H-NMR was conducted on an NMR spectrometer (Varian Unityionva 500 NMR Spectrometer, Mo.) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned from 400-4000 $cm^{-1}$. The average molecular weight of the purified γ-PGA was determined by the same GPC system as described before. Polyethylene glycol (molecular weights of 106-22,000) and polyethylene oxide (molecular weights of 20,000-1,000,000, PL Laboratories) standards were used to construct a calibration curve. The mobile phase contained 0.01M $NaH_2PO_4$ and 0.2M $NaNO_3$ and was brought to a pH of 7.0.

The purified γ-PGA obtained from fermentation was analyzed by GPC, $^1$H-NMR, and FT-IR. As analyzed by GPC (FIG. 1*b*), the purified γ-PGA had a MW of about 160 kDa. In the FT-IR spectrum (FIG. 2*a*), a characteristic peak at 1615 $cm^{-1}$ for the associated carboxylic acid salt (—$COO^-$ antisymmetric stretch) on γ-PGA was observed. The characteristic absorption due to C=O in secondary amides (amide I band) was overlapped by the characteristic peak of —$COO^-$. Additionally, the characteristic peak observed at 3400 $cm^{-1}$ was the N—H stretch of γ-PGA. In the $^1$H-NMR spectrum (FIG. 2*b*), six chief signals were observed at 1.73 and 1.94 ppm (β-$CH_2$), 2.19 ppm (γ-$CH_2$), 4.14 ppm (α-CH), 8.15 ppm (amide), and 12.58 ppm (COOH). These results indicated that the observed FT-IR and $^1$H-NMR spectra correspond well to those expected for γ-PGA. Additionally, the fermented product after purification showed no detected macromolecular impurities by the $^1$H-NMR analysis, suggesting that the obtained white power of γ-PGA is highly pure.

EXAMPLE NO. 4

Preparation of the CS-γ-PGA Nanoparticles

Nanoparticles were obtained upon addition of γ-PGA aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at varying concentrations (0.01%, 0.05%, 0.10%, 0.15%, or 0.20% by w/v) under magnetic stirring at room temperature. Nanoparticles were collected by ultracentrifugation at 38,000 rpm for 1 hour. Supernatants were discarded and nanoparticles were resuspended in deionized water for further studies. FT-IR was used to analyze peak variations of amino groups of low-MW CS and carboxylic acid salts of γ-PGA in the CS-γ-PGA nanoparticles.

Figure 3:
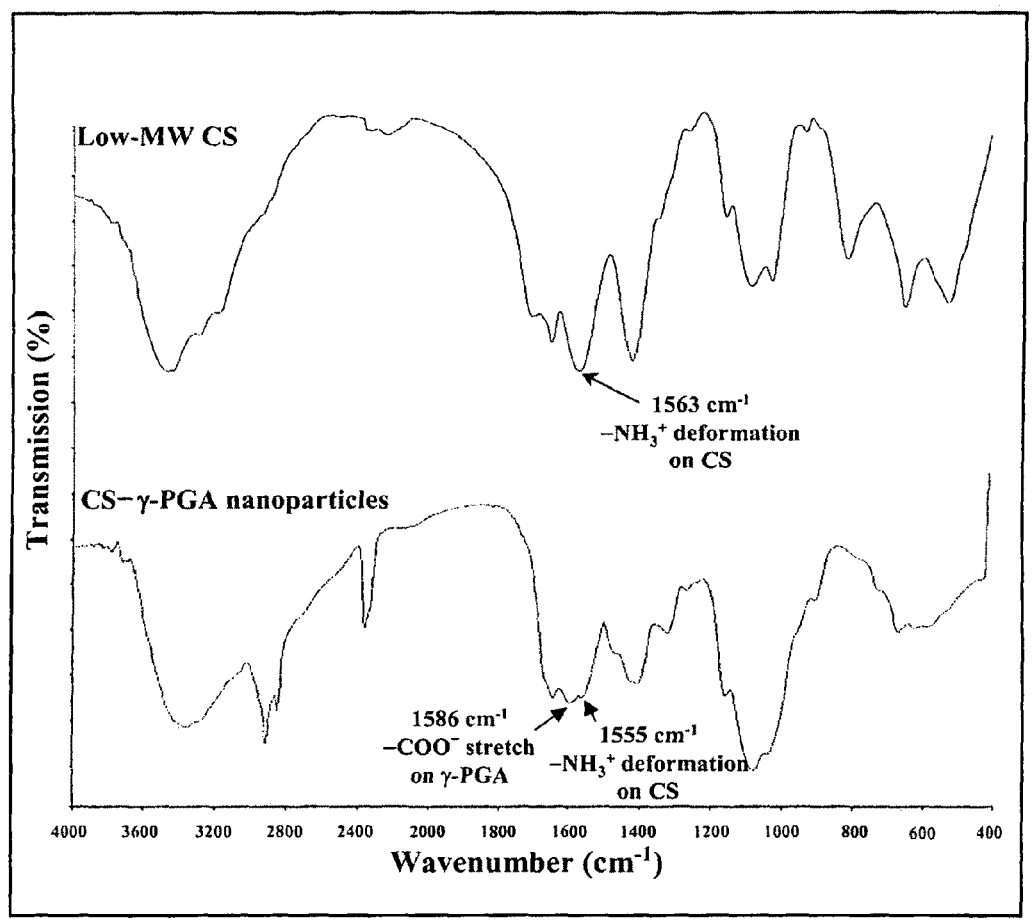
FIG. 3 shows FT-IR spectra of the low-MW CS and the prepared CS-γ-PGA nanoparticles.

As stated, nanoparticles were obtained instantaneously upon addition of a γ-PGA aqueous solution (pH 7.4) into a low-MW CS aqueous solution (pH 6.0) under magnetic stirring at room temperature. FIG. 3 shows the FT-IR spectra of the low-MW CS and the CS-γ-PGA nanoparticles. As shown in the spectrum of CS, the characteristic peak observed at 1563 $cm^{-1}$ was the protonated amino group (—$NH_3^+$ deformation) on CS. In the spectrum of CS-γ-PGA complex, the characteristic peak at 1615 $cm^{-1}$ for —$COO^{-1}$ on γ-PGA disappeared and a new peak at 1586 $cm^{-1}$ appeared, while the characteristic peak of —$NH_3^+$ deformation on CS at 1563 $cm^{-1}$ shifted to 1555 $cm^{-1}$. These observations are attributed to the electrostatic interaction between the negatively charged carboxylic acid salts (—$COO^-$) on γ-PGA and the positively charged amino groups (—$NH_3^+$) on CS (Int. J. Pharm. 2003; 250:215-226). The electrostatic interaction between the two polyelectrolytes (γ-PGA and CS) instantaneously induced the formation of long hydrophobic segments (or at least segments with a high density of neutral ion-pairs), and thus resulted in highly neutralized complexes that segregated into colloidal nanoparticles (Langmuir. 2004;20:7766-7778).

EXAMPLE NO. 5

Characterization of the CS-γ-PGA Nanoparticles

The morphological examination of the CS-γ-PGA nanoparticles was performed by TEM (transmission electron microscopy) and AFM (atomic force microscopy). The TEM sample was prepared by placing a drop of the nanoparticle solution onto a 400 mesh copper grid coated with carbon. About 2 minutes after deposition, the grid was tapped with a filter paper to remove surface water and positively stained by using an alkaline bismuth solution (Microbiol. Immunol. 1986;30:1207-121 1). The AFM sample was prepared by casting a drop of the nanoparticle solution on a slide glass and then dried in vacuum. The size distribution and zeta potential of the prepared nanoparticles were measured using a Zetasizer (3000HS, Malvern Instruments Ltd., Worcestershire, UK).

During storage, aggregation of nanoparticles may occur and thus leads to losing their structural integrity or forming precipitation of nanoparticles (Eur. J. Pharm. Sci. 1999;8:99-107). Therefore, the stability of nanoparticles during storage must be evaluated. In the stability study, the prepared nanoparticles suspended in deionized water (1 mg/ml) were stored at 4° C. and their particle sizes and zeta potential values were monitored by the same Zetasizer as mentioned earlier during storage.

In the preparation of nanoparticles, samples were visually analyzed and three distinct solution systems were identified: clear solution, opalescent suspension, and solution with precipitation of aggregates. Examined by the Zetasizer, nanoparticles were found in the clear solution and the opalescent suspension rather than in the solution with precipitation of aggregates.

The particle sizes and the zeta potential values of CS-γ-PGA nanoparticles, prepared at varying concentrations of γ-PGA and CS, were determined and the results are shown in Tables 1a and 1b. It was found that the particle size and the zeta potential value of the prepared nanoparticles were mainly determined by the relative amount of the local concentration of γ-PGA in the added solution to the surrounding concentration of CS in the sink solution. At a fixed concentration of CS, an increase in the γ-PGA concentration allowed γ-PGA molecules interacting with more CS molecules, and thus formed a lager size of nanoparticles (Table 1a, p<0.05). When the amount of CS molecules exceeded that of local γ-PGA molecules, some of the excessive CS molecules were entangled onto the surfaces of CS-γ-PGA nanoparticles.

Figure 4:
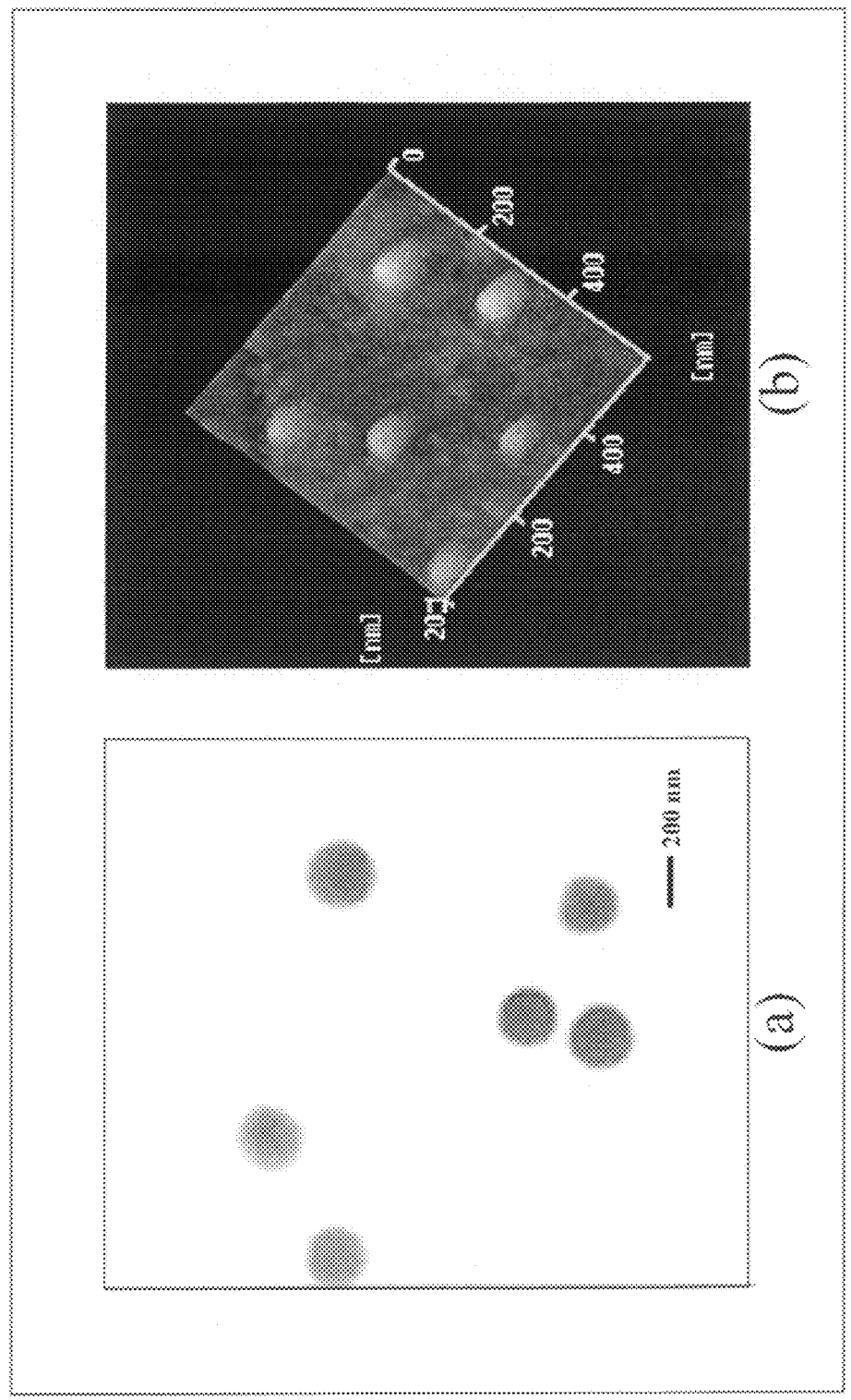
FIG. 4 shows (a) a TEM micrograph of the prepared CS-γ-PGA nanoparticles (0.10% γ-PGA:0.20% CS) and (b) an AFM micrograph of the prepared CS-γ-PGA nanoparticles (0.01% γ-PGA:0.01% CS).

Thus, the resulting nanoparticles may display a structure of a neutral polyelectrolyte-complex core surrounded by a positively charged CS shell (Table 1b) ensuring the colloidal stabilization (Langmuir. 2004;20:7766-7778). In contrast, as the amount of local γ-PGA molecules sufficiently exceeded that of surrounding CS molecules, the formed nanoparticles had γ-PGA exposed on the surfaces and thus had a negative charge of zeta potential. Therefore, the particle size and the zeta potential value of the prepared CS-γ-PGA nanoparticles can be controlled by their constituted compositions. The results obtained by the TEM and AFM examinations showed that the morphology of the prepared nanoparticles was spherical in shape with a smooth surface (FIGS. 4a and 4b). Some aspects of the invention relate to nanoparticles having a mean particle size between about 50 and 400 nanometers, preferably between about 100 and 300 nanometers, and most preferably between about 100 and 200 nanometers. The morphology of the nanoparticles shows spherical in shape with a smooth surface at any pH between 2.5 and 6.6. In one embodiment, the stability of the nanoparticles of the present invention at a low pH around 2.5 enables the nanoparticles to be intact when exposed to the acidic medium in the stomach.

Figure 5:
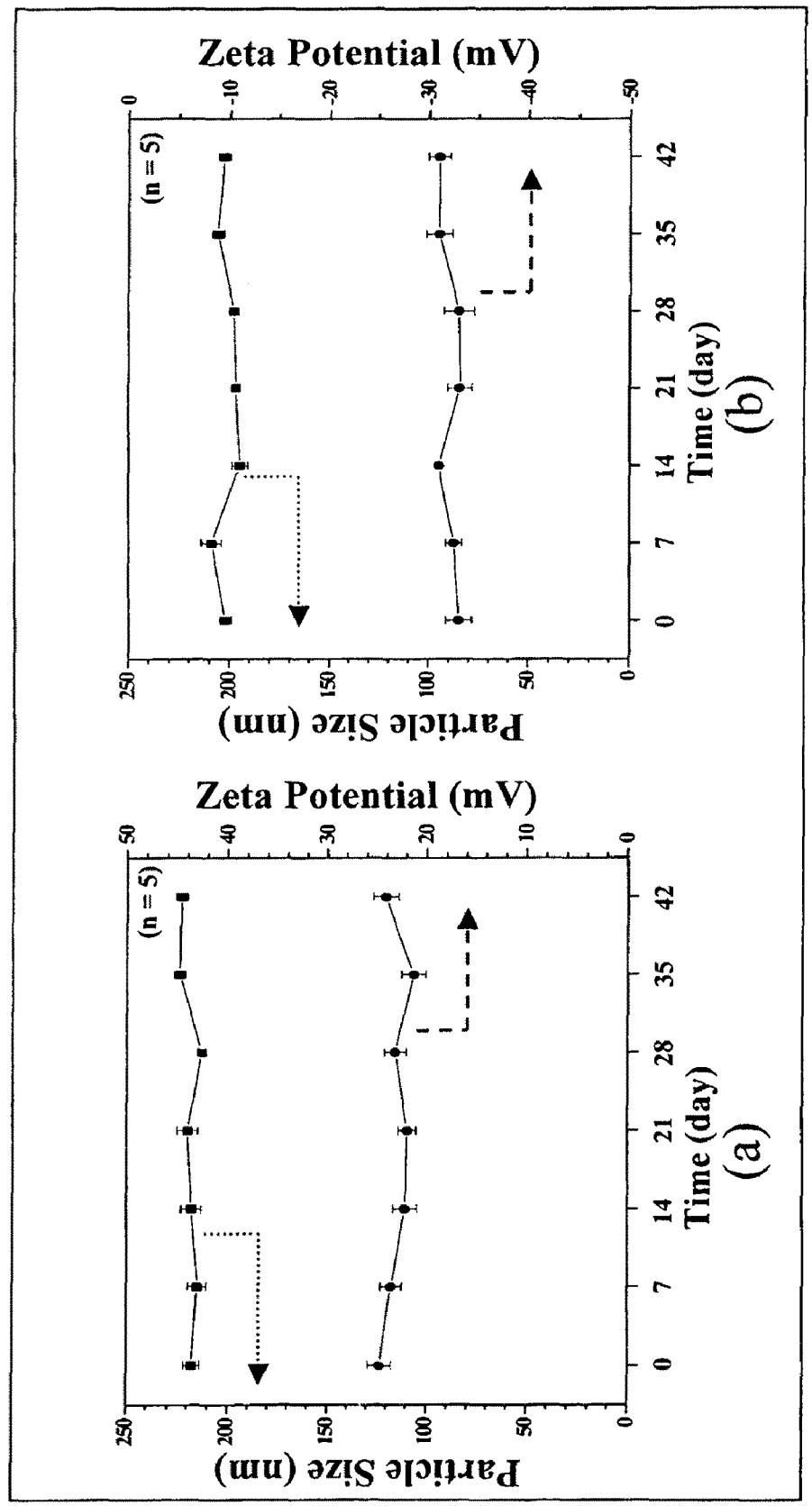
FIG. 5 shows changes in particle size and zeta potential of (a) the CS-γ-PGA nanoparticles (0.10% γ-PGA:0.20% CS) and (b) the CS-Y-PGA nanoparticles (0.10% γ-PGA:0.01% CS) during storage for up to 6 weeks.

Two representative groups of the prepared nanoparticles were selected for the stability study: one with a positive surface charge (0.10% γ-PGA:0.20% CS) and the other with a negative surface charge (0.10% γ-PGA:0.01% CS). FIG. 5 shows changes in particle size (■, mean diameter) and zeta potential (●) of (a) the CS-γ-PGA nanoparticles (0.10% γ-PGA:0.20% CS) and (b) the CS-γ-PGA nanoparticles (0.10% γ-PGA:0.01% CS) during storage for up to 6 weeks. It was found that neither aggregation nor precipitation of nanoparticles was observed during storage for up to 6 weeks, as a result of the electrostatic repulsion between the positively charged CS-γ-PGA nanoparticles (for the former group) or the negatively charged CS-γ-PGA nanoparticles (for the latter group).

Additionally, changes in particle size and zeta potential of the nanoparticles were minimal for both studied groups (FIGS. 5a and 5b). These results demonstrated that the prepared nanoparticles suspended in deionized water were stable during storage.

EXAMPLE NO. 6

Caco-2 Cell Cultures and TEER Measurements

Caco-2 cells were seeded on the tissue-culture-treated polycarbonate filters (diameter 24.5 mm, growth area 4.7 $cm^2$) in Costar Transwell 6 wells/plates (Corning Costar Corp., NY) at a seeding density of $3\times10^5$ cells/insert. MEM (pH 7.4) supplemented with 20% FBS, 1% NEAA, and 40 μg/ml antibiotic-gentamicin was used as the culture medium, and TABLE 1a Effects of concentrations of γ-PGA and CS on the particle sizes of the prepared CS-γ-PGA nanoparticles
Mean Particle Size (nm, n = 5)

| γ-PGA | CS | | | | |
|---|---|---|---|---|---|
| | 0.01%[a] | 0.05% | 0.10% | 0.15% | 0.20% |
| 0.01%[b] | 79.0 ± 3.0 | 103.1 ± 4.6 | 96.7 ± 1.9 | 103.6 ± 1.9 | 140.5 ± 2.0 |
| 0.05% | 157.4 ± 1.7 | 120.8 ± 3.9 | 144.5 ± 2.4 | 106.2 ± 3.8 | 165.4 ± 1.7 |
| 0.10% | 202.2 ± 3.1 | 232.6 ± 1.2 | 161.0 ± 1.8 | 143.7 ± 2.7 | 218.1 ± 4.1 |
| 0.15% | 277.7 ± 3.2 | 264.9 ± 2.1 | 188.6 ± 2.9 | 178.0 ± 2.2 | 301.1 ± 6.4 |
| 0.20% | 284.1 ± 2.1 | 402.2 ± 4.0 | ▲ | 225.5 ± 3.1 | 365.5 ± 5.1 |

[a] concentration of CS (by w/v)
[b] concentration of γ-PGA (by w/v)
▲ precipitation of aggregates was observed TABLE 1b Effects of concentrations of γ-PGA and CS on the zeta potential values of the prepared CS-γ-PGA nanoparticles.
Zeta Potential (mV, n = 5)

| γ-PGA | CS | | | | |
|---|---|---|---|---|---|
| | 0.01%[a] | 0.05% | 0.10% | 0.15% | 0.20% |
| 0.01%[b] | 15.4 ± 0.3 | 22.8 ± 0.5 | 19.8 ± 1.5 | 16.5 ± 1.4 | 17.2 ± 1.6 |
| 0.05% | −32.7 ± 0.7 | 23.7 ± 1.7 | 27.6 ± 0.7 | 20.3 ± 0.8 | 19.2 ± 0.6 |
| 0.10% | −33.1 ± 1.3 | 21.1 ± 1.6 | 20.3 ± 1.1 | 23.6 ± 0.9 | 24.7 ± 1.2 |
| 0.15% | −33.2 ± 2.1 | −21.9 ± 2.0 | 19.2 ± 0.4 | 16.9 ± 1.7 | 19.8 ± 0.3 |
| 0.20% | −34.5 ± 0.5 | −34.6 ± 0.3 | ▲ | 14.6 ± 0.7 | 16.3 ± 0.7 |

[a] concentration of CS (by w/v)
[b] concentration of γ-PGA (by w/v)
▲ precipitation of aggregates was observed added to both the donor and acceptor compartments. The medium was replaced every 48 hours for the first 6 days and every 24 hours thereafter. The cultures were kept in an atmosphere of 95% air and 5% $CO_2$ at 37° C. and were used for the paracellular transport experiments 18-21 days after seeding (TEER values in the range of 600-800 $\Omega cm^2$).

TEER values of the Caco-2 cell monolayers were monitored with a Millicell®-Electrical Resistance System (Millipore Corp., Bedford, Mass.) connected to a pair of chopstick electrodes. To initiate the transport experiments, the culture media in the donor and acceptor compartments were aspirated, and the cells were rinsed twice with pre-warmed transport media (HBSS supplemented with 25 mM glucose, pH 6.0). Following a 30-min equilibration with the transport media at 37° C., the cells were incubated for 2 hours with 2 ml transport media containing 0.5 ml test nanoparticle solutions (0.2 mg/ml) at 37° C. Subsequently, solutions of nanoparticles were carefully removed and cells were washed three times with HBSS and replaced by fresh culture media. The TEER was measured for another 20 hours to study reversibility of the effect of test nanoparticles on Caco-2 cell monolayers (Eur. J. Pharm. Sci. 2000;10:205-214).

The intercellular tight junction is one of the major barriers to the paracellular transport of macromolecules (J. Control. Release 1996;39:131-138; J. Control. Release 1998;51:35-46). Trans-epithelial ion transport is contemplated to be a good indication of the tightness of the junctions between cells and was evaluated by measuring TEER of Caco-2 cell monolayers in the study. It was reported that the measurement of TEER can be used to predict the paracellular transport of hydrophilic molecules (Eur. J. Pharm. Biopharm. 2004;58:225-235). When the tight junctions open, the TEER value will be reduced due to the water and ion passage through the paracellular route. Caco-2 cell monolayers have been widely used as an in vitro model to evaluate the intestinal paracellular permeability of macromolecules.

Figure 6:
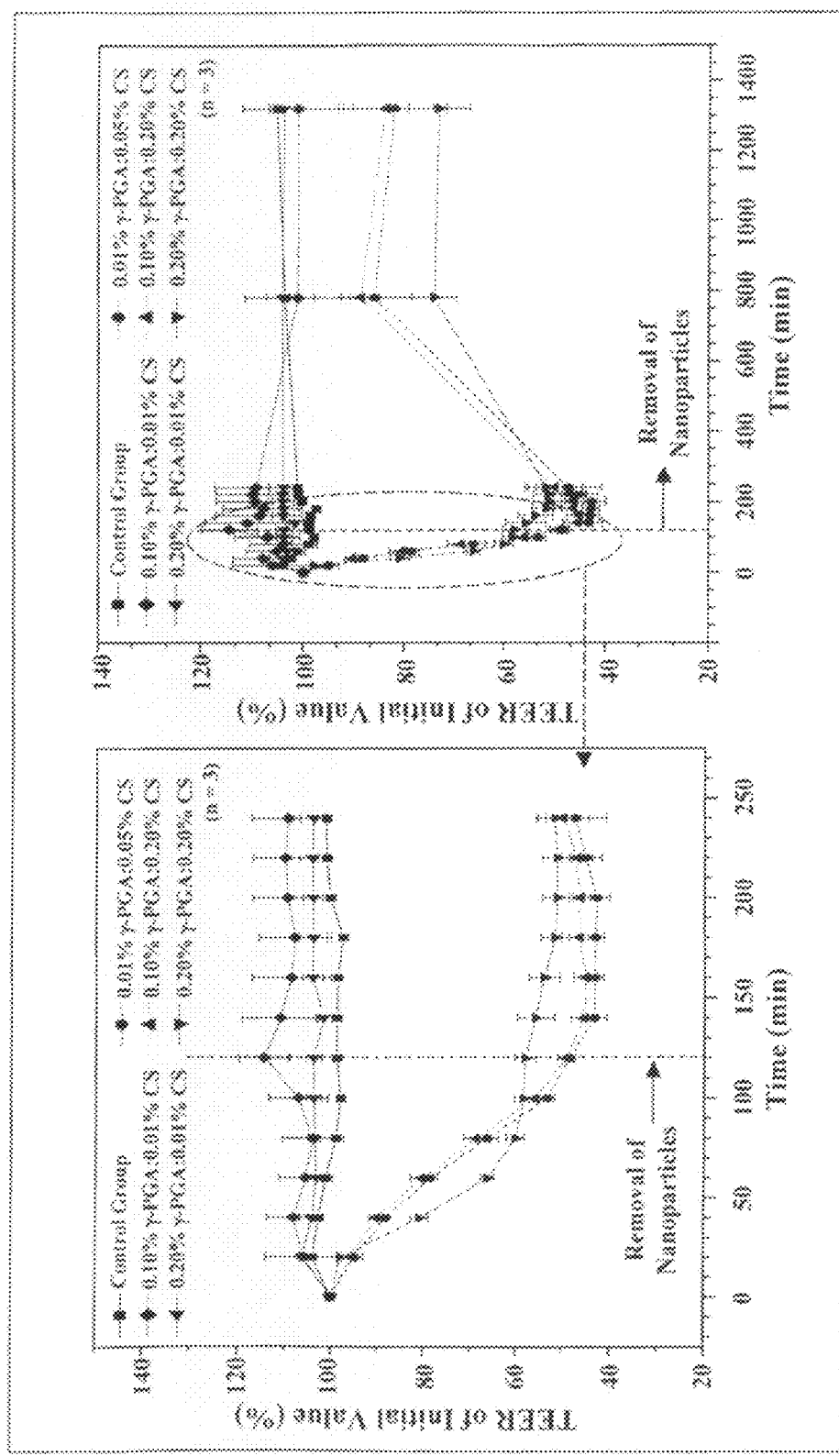
FIG. 6 shows effects of the prepared CS-γ-PGA nanoparticles on the TEER values of Caco-2 cell monolayers.

Effects of the prepared CS-γ-PGA nanoparticles on the TEER values of Caco-2 cell monolayers are shown in FIG. 6. As shown, the prepared nanoparticles with a positive surface charge (CS dominated on the surface, 0.01% γ-PGA:0.05% CS, 0.10% γ-PGA:0.2% CS, and 0.20% γ-PGA:0.20% CS) were able to reduce the values of TEER of Caco-2 cell monolayers significantly (p<0.05). After a 2-hour incubation with these nanoparticles, the TEER values of Caco-2 cell monolayers were reduced to about 50% of their initial values as compared to the control group (without addition of nanoparticles in the transport media). This indicated that the nanoparticles with CS dominated on the surfaces could effectively open the tight junctions between Caco-2 cells, resulting in a decrease in the TEER values. It was reported that interaction of the positively charged amino groups of CS with the negatively charged sites on cell surfaces and tight junctions induces a redistribution of F-actin and the tight junction's protein ZO-1, which accompanies the increased paracellular permeability (Drug Deliv. Rev. 2001;50:S91-S101). It is suggested that an interaction between chitosan and the tight junction protein ZO-1, leads to its translocation to the cyto skeleton.

After removal of the incubated nanoparticles, a gradual increase in TEER values was noticed. This phenomenon indicated that the intercellular tight junctions of Caco-2 cell monolayers started to recover gradually; however, the TEER values did not recover to their initial values (FIG. 6). Kotzé et al. reported that complete removal of a CS-derived polymer, without damaging the cultured cells, was difficult due to the highly adhesive feature of CS (Pharm. Res. 1997;14:1197-1202). This might be the reason why the TEER values did not recover to their initial values. In contrast, the TEER values of Caco-2 cell monolayers incubated with the nanoparticles with a negative surface charge (γ-PGA dominated on the surface, 0.10% γ-PGA:0.01% CS and 0.20% γ-PGA:0.01% CS, FIG. 6) showed no significant differences as compared to the control group (p>0.05). This indicated that γ-PGA does not have any effects on the opening of the intercellular tight junctions.

Figure 8:
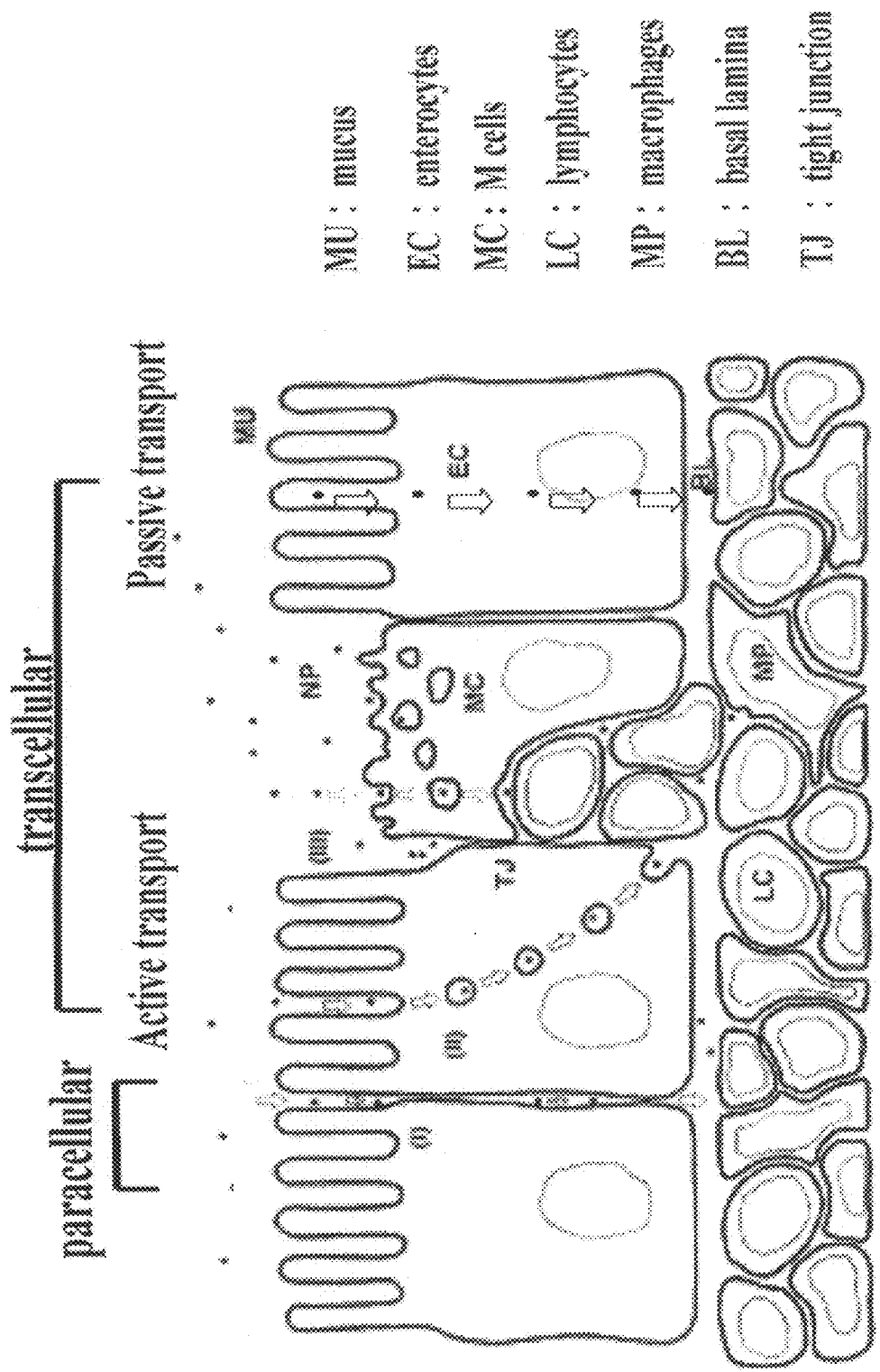
FIG. 8 shows an illustrative protein transport mechanism through a cell layer, including transcellular transport and paracelluler transport.
Figure 9:
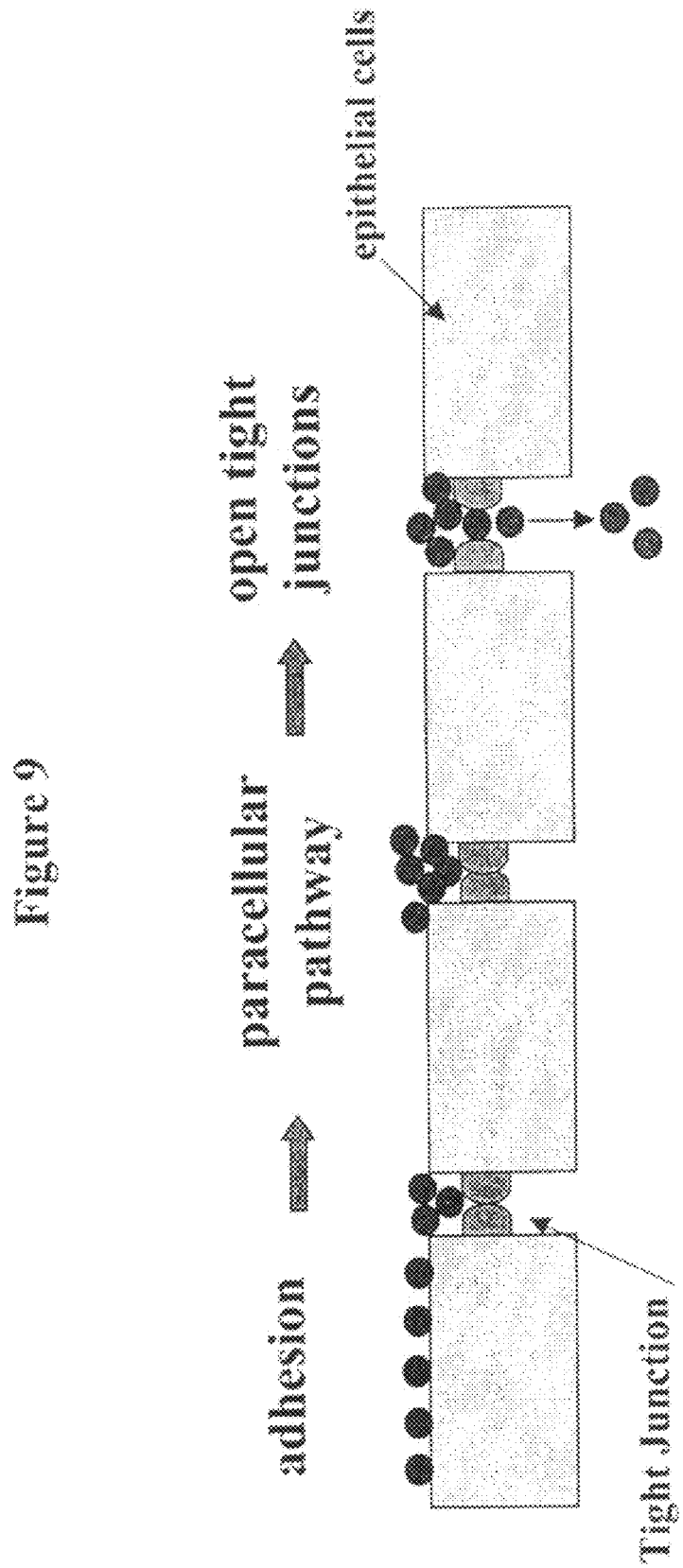
FIG. 9 shows a schematic illustration of a paracellular transport mechanism.

FIG. 8 shows an illustrative protein transport mechanism through a cellular layer, including transcellular transport and paraculler transport. FIG. 9 shows a schematic illustration of a paracellular transport mechanism. The transcellular protein or peptide transport may be an active transport or a passive transport mode whereas the paracellular transport is basically a passive mode. Ward et al. reported and reviewed current knowledge regarding the physiological regulation of tight junctions and paracellular permeability (PSTT 2000;3:346-358). Chitosan as nanoparticle vehicles for oral delivery of protein drugs avoids the enzymatic inactivation in the gastrointestinal conduit. The chitosan component of the present nanoparticles has a special feature of adhering to the mucosal surface and transiently opening the tight junctions between epithelial cells. The mucoadhesive CS-shelled nanoparticles can prolong their residence in the intestine and mediate transient opening of the tight junctions of epithelial cells, thereby facilitating the encapsulated nanoparticles crossing the epithelium barrier and enhancing the intestinal absorption of drugs.

EXAMPLE NO. 7 fCS-γ-PGA Nanoparticle Preparation and CLSM Visualization

Figure 10:
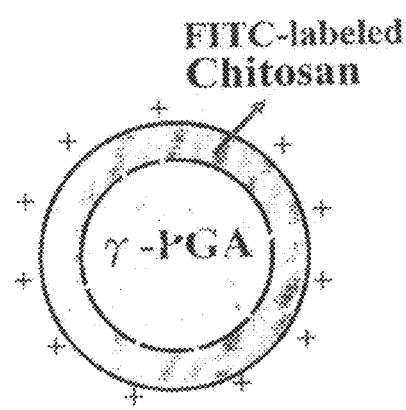
FIG. 10 shows an fCS-γ-PGA nanoparticle with FITC-labeled chitosans having positive surface charge.

Fluorescence (FITC)-labeled CS-γ-PGA (fCS-γ-PGA) nanoparticles (FIG. 10) were prepared for the confocal laser scanning microscopy (CLSM) study. The nanoparticles of the present invention display a structure of a neutral polyelectrolyte-complex core surrounded by a positively charged chitosan shell. Synthesis of the FITC-labeled low-MW CS (fCS) was based on the reaction between the isothiocyanate group of FITC and the primary amino groups of CS as reported in the literature (Pharm. Res. 2003;20:1812-1819). Briefly, 100 mg of FITC in 150 ml of dehydrated methanol were added to 100 ml of 1% low-MW CS in 0.1M acetic acid. After 3 hours of reaction in the dark at ambient conditions, fCS was precipitated by raising the pH to about 8-9 with 0.5M NaOH. To remove the unconjugated FITC, the precipitate was subjected to repeated cycles of washing and centrifugation (40,000× g for 10 min) until no fluorescence was detected in the supernatant. The fCS dissolved in 80 ml of 0.1 M acetic acid was then dialyzed for 3 days in the dark against 5 liters of distilled water, with water replaced on a daily basis. The resultant fCS was lyophilized in a freeze dryer. The fCS-γ-PGA nanoparticles were prepared as per the procedure described in Example No. 4.

Subsequently, the transport medium containing fCS-γ-PGA nanoparticles (0.2 mg/ml) was introduced into the donor compartment of Caco-2 cells, which were pre-cultured on the transwell for 18-21 days. The experimental temperature was maintained at 37° C. by a temperature control system (DH-35 Culture Dish Heater, Warner Instruments Inc., Hamden, Conn.). After incubation for specific time intervals, test samples were aspirated. The cells were then washed twice with pre-warmed PBS solution before they were fixed in 3.7% paraformaldehyde (Pharm. Res. 2003;20:1812-1819). Cells were examined under an inversed CLSM (TCS SL, Leica, Germany). The fluorescence images were observed using an argon laser (excitation at 488 nm, emission collected at a range of 510-540 nm).

Figure 7:
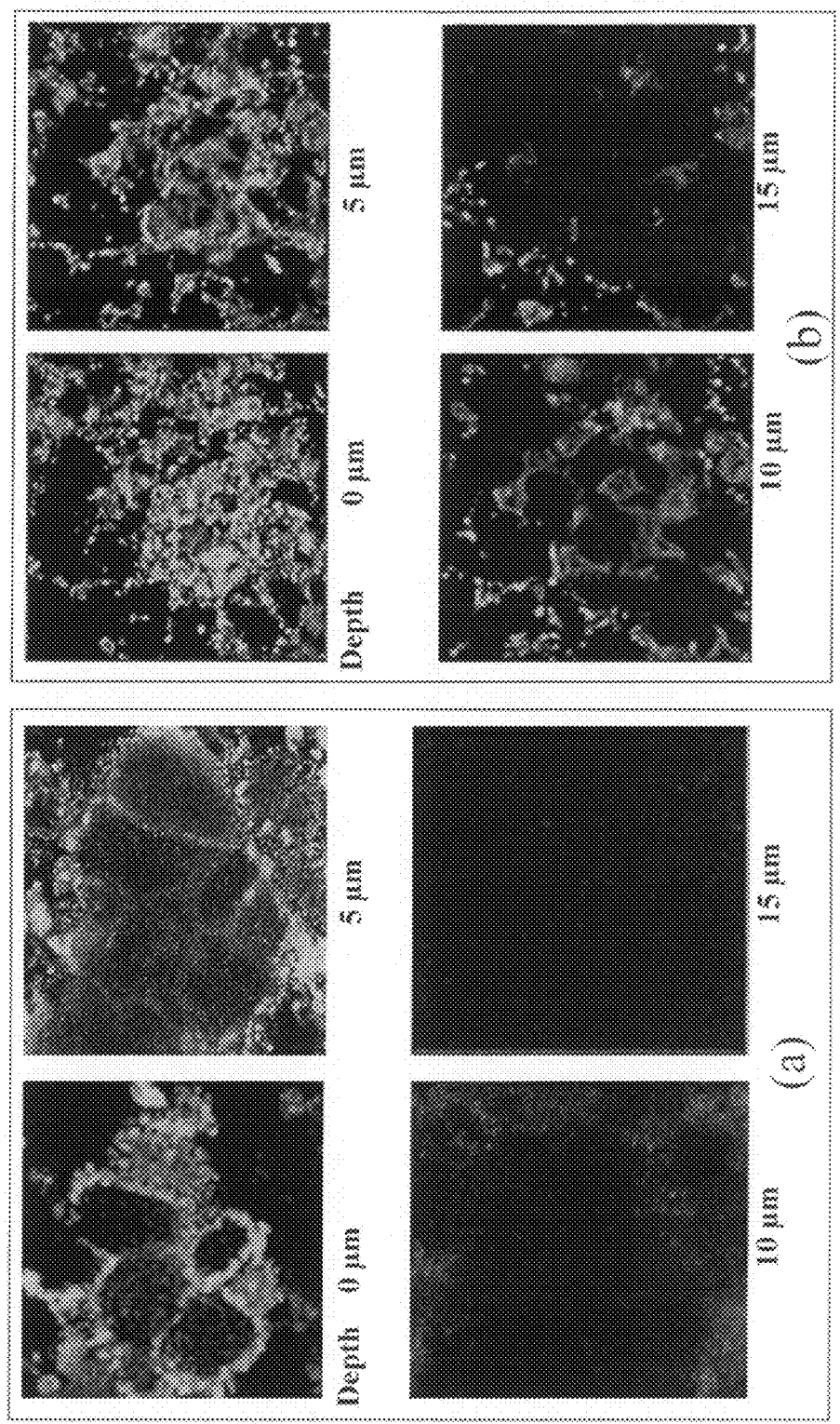
FIG. 7 shows fluorescence images (taken by an inversed confocal laser scanning microscope) of 4 optical sections of a Caco-2 cell monolayer that had been incubated with the fCS-γ-PGA nanoparticles with a positive surface charge (0.10% γ-PGA:0.20% CS) for (a) 20 min and (b) 60 min.

CLSM was used to visualize the transport of the fluorescence-labeled CS-γ-PGA (fCS-γ-PGA) nanoparticles across the Caco-2 cell monolayers. This non-invasive method allows for optical sectioning and imaging of the transport pathways across the Caco-2 cell monolayers, without disrupting their structures (J. Control. Release 1996;39:131-138). FIGS. 7a and 7b show the fluorescence images of 4 optical sections of a Caco-2 cell monolayer that had been incubated with the fCS-γ-PGA nanoparticles having a positive surface charge (0.10% γ-PGA:0.20% CS, zeta potential: about 21 mV) for 20 and 60 min, respectively. As shown, after 20 min of incubation with the nanoparticles, intense fluorescence signals at intercellular spaces were observed at depths of 0 and 5 µm from the apical (upper) surface of the cell monolayer. The intensity of fluorescence became weaker at levels deeper than 10 µm from the apical surface of the cell monolayer and was almost absent at depths $\geq 15$ µm (FIG. 7a).

After 60 minutes of incubation with the nanoparticles, the intensity of fluorescence observed at intercellular spaces was stronger and appeared at a deeper level than those observed at 20 min after incubation. These observations confirmed with our TEER results that the nanoparticles with a positive surface charge (CS dominated on the surface) were able to open the tight junctions between Caco-2 cells and allowed transport of the nanoparticles by passive diffusion via the paracellular pathways.

EXAMPLE NO. 8

In Vivo Study With Fluorescence-Labeled Nanoparticles

Fluorescence (FITC)-labeled CS-γ-PGA (fCSγ-PGA) nanoparticles were prepared for the confocal laser scanning microscopy (CLSM) study. After feeding rats with fCS-γ-PGA nanoparticles, the rats are sacrificed at a pre-determined time and the intestine is isolated for CLSM examination. The fluorescence images of the nanoparticles were clearly observed by CLSM that penetrates through the mouse intestine at appropriate time and at various depths from the inner surface toward the exterior surface of the intestine, including duodenum, jejunum, and ileum.

EXAMPLE NO. 9

Insulin Loading Capacity in Nanoparticles

Fluorescence (FITC)-labeled γ-PGA was added into chitosan solution to prepare fluorescence (FITC)-labeled, insulin-loaded CS-γ-PGA nanoparticles for in vivo animal study with confocal laser scanning microscopy (CLSM) assessment and bioactivity analysis. The insulin-loaded CS-γ PGA nanoparticles are by using the ionic-gelation method upon addition of insulin mixed with γ-PGA solution into CS solution, followed by magnetic stirring in a container.

Model insulin used in the experiment and disclosed herein is obtained from bovine pancreas (Sigma-Aldrich, St. Louis, Mo.), having a molecular formula of $C_{254}H_{377}N_{65}O_{75}S_6$ with a molecular weight of about 5733.5 and an activity of $\geq 27$ USP units/mg. The insulin contains two-chain polypeptide hormone produced by the β-cells of pancreatic islets. The α and β chains are joined by two interchain disulfide bonds. Insulin regulates the cellular uptake, utilization, and storage of glucose, amino acids, and fatty acids and inhibits the breakdown of glycogen, protein, and fat. The insulin from Sigma-Aldrich contains about 0.5% zinc. Separately, insulin can be obtained from other sources, such as human insulin solution that is chemically defined, recombinant from Saccharomyces cerevisiae. Some aspects of the invention relate to nanoparticles with insulin in the core, wherein the insulin may contain intermediate-acting, regular insulin, rapid-acting insulin, sustained-acting insulin that provides slower onset and longer duration of activity than regular insulin, or combinations thereof.

Examples of insulin or insulin analog products include, but not limited to, Humulin® (by Eli Lilly), Humalog® (by Eli Lilly) and Lantus® (by Aventis), and Novolog® Mix70/30 (by Novo Nordisk). Humalog (insulin lispro, rDNA origin) is a human insulin analog that is a rapid-acting, parenteral blood glucose-lowering agent. Chemically, it is Lys(B28), Pro(B29) human insulin analog, created when the amino acids at positions 28 and 29 on the insulin B-chain are reversed. Humalog is synthesized in a special non-pathogenic laboratory strain of *Escherichia coli* bacteria that has been genetically altered by the addition of the gene for insulin lispro. Humalog has the empirical formula $C_{257}H_{383}N_{65}O_{77}S_6$ and a molecular weight of 5808, identical to that of human insulin. The vials and cartridges contain a sterile solution of Humalog for use as an injection. Humalog injection consists of zinc-insulin lispro crystals dissolved in a clear aqueous fluid. Each milliliter of Humalog injection contains insulin lispro 100 Units, 16 mg glycerin, 1.88 mg dibasic sodium phosphate, 3.15 mg m-cresol, zinc oxide content adjusted to provide 0.0197 mg zinc ion, trace amounts of phenol, and water for injection. Insulin lispro has a pH of 7.0-7.8. Hydrochloric acid 10% and/or sodium hydroxide 10% may be added to adjust pH.

Humulin is used by more than 4 million people with diabetes around the world every day. Despite its name, this insulin does not come from human beings. It is identical in chemical structure to human insulin and is made in a factory using a chemical process called recombinant DNA technology. Humulin L is an amorphous and crystalline suspension of human insulin with a slower onset and a longer duration of activity (up to 24 hours) than regular insulin. Humulin U is a crystalline suspension of human insulin with zinc providing a slower onset and a longer and less intense duration of activity (up to 28 hours) than regular insulin or the intermediate-acting insulins (NPH and Lente).

LANTUS® (insulin glargine [rDNA origin] injection) is a sterile solution of insulin glargine for use as an injection. Insulin glargine is a recombinant human insulin analog that is a long-acting (up to 24-hour duration of action), parenteral blood-glucose-lowering agent. LANTUS is produced by recombinant DNA technology utilizing a non-pathogenic laboratory strain of *Escherichia coli* (K12) as the production organism. Insulin glargine differs from human insulin in that the amino acid asparagine at position A21 is replaced by glycine and two arginines are added to the C-terminus of the B-chain. Chemically, it is $21^A$-Gly-$30^B$a-L-Arg-$30^B$b-L-Arg-human insulin and has the empirical formula $C_{267}H_{404}N_{72}O_{78}S_6$ and a molecular weight of 6063.

LANTUS consists of insulin glargine dissolved in a clear aqueous fluid. Each milliliter of LANTUS (insulin glargine injection) contains 100 IU (3.6378 mg) insulin glargine. Inactive ingredients for the 10 mL vial are 30 mcg zinc, 2.7 mg m-cresol, 20 mg glycerol 85%, 20 mcg polysorbate 20, and water for injection. Inactive ingredients for the 3 mL cartridge are 30 mcg zinc, 2.7 mg m-cresol, 20 mg glycerol 85%, and water for injection.

Novolog® Mix70/30 (70% insulin aspart protamine suspension and 30% insulin aspart injection [rDNA origin]) is a human insulin analog suspension. Novolog® Mix70/30 is a blood glucose-lowering agent with a rapid onset and an intermediate duration of action. Insulin aspart is homologous with regular human insulin with the exception of a single substitution of the amino acid praline by aspartic acid in position B28, and is produced by recombinant DNA technology utilizing *Saccharomyces cerevisiae* as the production organism. Insulin aspart (Novolog) has the empirical formula $C_{256}H_{381}N_{65}O_{79}S_6$ and a molecular weight of 5826. Novolog® Mix70/30 is a uniform, white sterile suspension that contains zinc 19.6 µg/ml and other components.

The nanoparticles with two insulin concentrations are prepared at a chitosan to γ-PGA ratio of 0.75 mg/ml to 0.167 mg/ml. Their particle size and zeta potential are shown in Table 2 below.

TABLE 2

| Insulin Conc. (mg/ml) (n = 5) | Mean Particle Size (nm) | Polydispersity Index (PI) | Zeta Potential (mV) |
|---|---|---|---|
| 0* | 145.6 ± 1.9 | 0.14 ± 0.01 | +32.11 ± 1.61 |
| 0.042 | 185.1 ± 5.6 | 0.31 ± 0.05 | +29.91 ± 1.02 |
| 0.083 | 198.4 ± 6.2 | 0.30 ± 0.09 | +27.83 ± 1.22 |

*control reference without insulin

Figure 11:
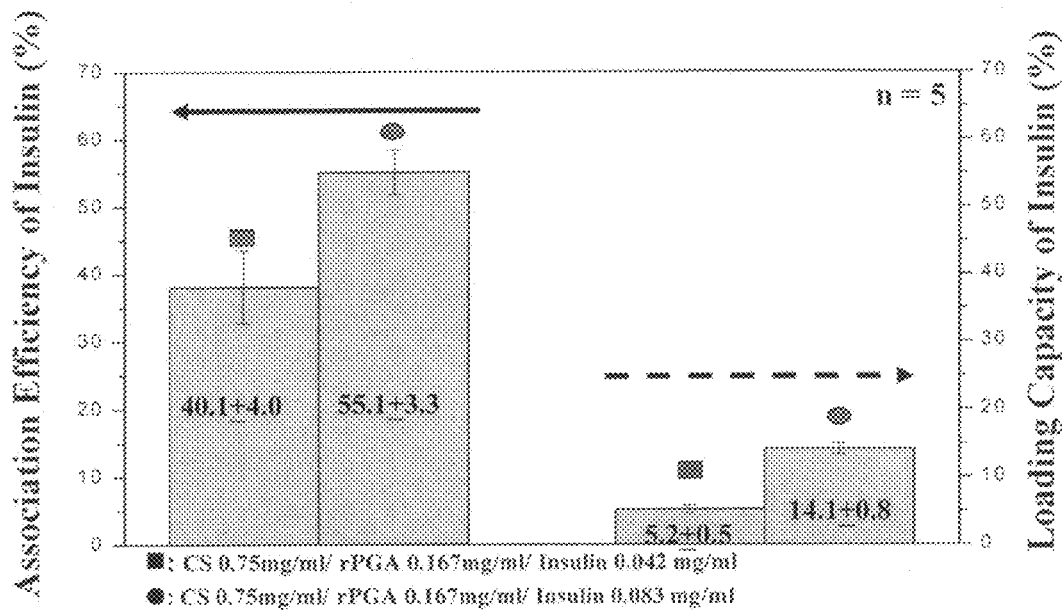
FIG. 11 shows loading capacity and association efficiency of insulin in nanoparticles of chitosan and γ-PGA.
Figure 12:
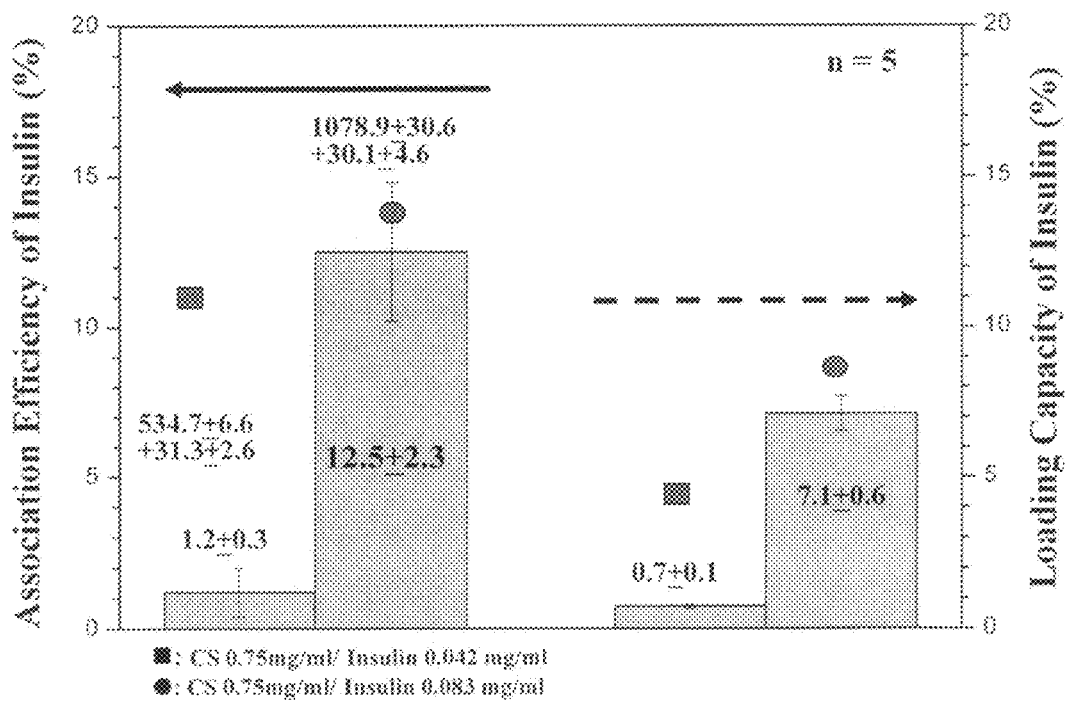
FIG. 12 shows loading capacity and association efficiency of insulin in nanoparticles of chitosan as reference.

Further, their association efficiency of insulin and loading capacity of insulin are analyzed, calculated and shown in FIGS. 11 and 12, according to the following formula:

$$\text{Insulin Association Efficiency } (AE\ \%) = \frac{\text{(Total amount of insulin} - \text{Insulin in supernatant)}}{\text{Total amount of insulin}} \times 100\%$$

$$\text{Loading Capacity } (LC) = \frac{\text{(Total amount of insulin} - \text{Insulin in supernatant)}}{\text{Weight of recovered particles}} \times 100\%$$

FIG. 11 shows loading capacity and association efficiency of insulin in nanoparticles of chitosan and γ-PGA, whereas FIG. 12 shows loading capacity and association efficiency of insulin in nanoparticles of chitosan alone (in absence of γ-PGA) as reference. The data clearly demonstrates that both the insulin loading capacity and insulin association efficiency are statistically higher for the nanoparticles with γ-PGA in the core. The AE (40~55%) and LC (5.0~14.0%) of insulin for CS-γ PGA nanoparticles was obtained by using ionic-gelation method upon addition of insulin mixed with γ-PGA solution into CS solution, followed by magnetic stirring for nanoparticle separation. Some aspects of the invention relate to an oral dose of nanoparticles that effectively enhance intestinal or blood brain paracellular transport comprising a negative component (such as γ-PGA, α-PGA, PGA derivatives, heparin, or alginate) in the core and low molecular weight chitosan, wherein the chitosan dominates on a surface of the nanoparticles with positive charges.

EXAMPLE NO. 10

Insulin Loading in PGA Nanoparticles

The nanoparticles with two core substrates (γ-PGA and α-PGA) are prepared at a chitosan to PGA ratio of 0.75 mg/ml to 0.167 mg/ml with insulin concentration at 0.083 mg/ml (sample size, n=3). Their particle size, zeta potential, and insulin loading efficiency are quite comparable and are shown in Table 3 below.

TABLE 3

| Core Substrate | Mean Particle Size (nm) | Polydispersity Index (PI) | Zeta Potential (mV) | Loading Efficiency (%) |
|---|---|---|---|---|
| γ-PGA | 218.4 ± 5.2 | 0.32 ± 0.09 | +25.4 ± 1.22 | 52.1 ± 4.3 |
| α-PGA | 207.6 ± 9.3 | 0.29 ± 0.07 | +26.8 ± 1.01 | 59.1 ± 5.0 |

Some aspects of the invention relate to a dose of nanoparticles that effectively enhance intestinal or blood brain paracellular transport comprising a polyanionic component (such as γ-PGA, α-PGA, PGA derivatives, heparin, heparin analogs, low molecular weight heparin, glycosaminoglycans, or alginate) in the core and low molecular weight chitosan in the shell, wherein the chitosan dominates on a surface of the nanoparticles with surface positive charges. In use, firstly, encapsulate the Alzheimer's drug in the chitosan shell nanoparticle as described herein, wherein the nanoparticle is partially crosslinked (optionally) to enhance its biodurability. Then intra-venously inject the nanoparticles, whereby the nanoparticles pass to the brain in blood circulation. The chitosan shell of the nanoparticles adheres to the surface adjacent the tight junction in the brain. Thereafter, the chitosan nanoparticle opens the tight junction, wherein the Alzheimer's drug is released after passing the tight junction for therapeutic treatment. In one embodiment, the nanoparticles are in a spherical shape having a mean particle size of about 50 to 250 nanometers, preferably 150 nanometers to 250 nanometers.

In one example, intravenous administration of the nanoparticles comprising chitosan shell substrate, polyanionic core substrate and at least one bioactive agent for treating Alzheimer's disease in a patient is typically performed with 10 mg to 40 mg of active agent per day over a period of one month to one year. The bioactive agent is selected from a group consisting of donepezile, rivastignine, galantamine, and/or those trade-named products, such as memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), and tacrine hydrochloride (Cognex® by Parke Davis).

Some aspects of the invention relate to a nanoparticle with a core substrate comprising polyglutamic acids such as water soluble salt of polyglutamic acids (for example, ammonium salt) or metal salts of polyglutamic acid (for example, lithium salt, sodium salt, potassium salt, magnesium salt, and the like). In one embodiment, the form of polyglutamic acid may be selected from a group consisting of poly-α-glutamic acid, poly-L-α-glutamic acid, poly-γ-glutamic acid, poly-D-glutamic acid, poly-y-D-glutamic acid, poly-γ-DL-glutamic acid, poly-L-glutamic acid (manufactured by Sigma-Aldrich, St. Louis, Mo.), and PEG or PHEG derivatives of polyglutamic acid. Alginate is generally non-biodegradable; however, it is stipulated that an alginate particle with about 30-50 kDa molecular weight is kidney inert. Heparin with negatively charged side-groups has a general chemical structure as shown below:

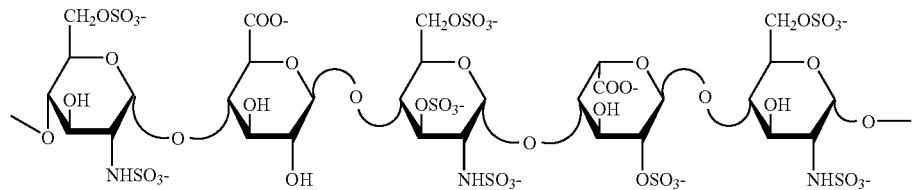

Some aspects of the invention relate to the negatively charged glycosaminoglycans (GAGs) as the core substrate of the present nanoparticles. GAGs may be used to complex with a low-molecular-weight chitosan to form drug-carrier nanoparticles. GAGs may also conjugate with the proteins (for example, monoclonal antibodies) as disclosed herein to enhance the bonding efficiency of the core substrate in the nanoparticles. Particularly, the negatively charged core substrate (such as GAGs, heparin, PGA, alginate, and the like) of the nanoparticles of the present invention may conjugate with chondroitin sulfate, hyaluronic acid, PDGF-BB, BSA, EGF, MK, VEGF, KGF, bFGF, aFGF, MK, PTN, etc.

Calceti et al. reported an in vivo evaluation of an oral insulin-PEG delivery system (Eur J Pharma Sci 2004;22:315-323). Insulin-PEG was formulated into mucoadhesive tablets constituted by the thiolated polymer poly(acrylic acid)-cysteine. The therapeutic agent was sustained released from these tablets within 5 hours. In vivo, by oral administration to diabetic mice, the glucose levels were found to decrease significantly over the time. Further, Krauland et al. reported another oral insulin delivery study of thiolated chitosan-insulin tablets on non-diabetic rats (J. Control. Release 2004, 95:547-555). The delivery tablets utilized 2-Iminothiolane covalently linked to chitosan to form chitosan-TBA (chitosan-4-thiobutylamidine) conjugate. After oral administration of chitosan-TBA-insulin tablets to non-diabetic conscious rats, the blood glucose level decreased significantly for 24 hours; supporting the observation of sustained insulin release of the presently disclosed nanoparticles herein through intestinal absorption. In a further report by Morcol et al. (Int. J. Pharm. 2004;277:91-97), an oral delivery system comprising calcium phosphate-PEG-insulin-casein particles displays a prolonged hypoglycemic effect after oral administration to diabetic rats.

Pan et al. disclosed chitosan nanoparticles improving the intestinal absorption of insulin in vivo (Int J Pharma 2002; 249:139-147) with insulin-chitosan nanoparticles at a particle size of 250-400 nm, a polydispersity index smaller than 0.1, positively charged and stable. After administering the insulin-chitosan nanoparticles, it was found that the hypoglycemic was prolonged with enhanced pharmacological bioavailability. Their data confirmed our observation as shown in FIGS. 11 and 12; however, the insulin loading capacity and insulin association efficiency of the present invention are substantially higher for the chitosan-insulin nanoparticles with γ-PGA in the core as the core substrate.

EXAMPLE NO. 11

Insulin Nanoparticle Stability

Figure 13:
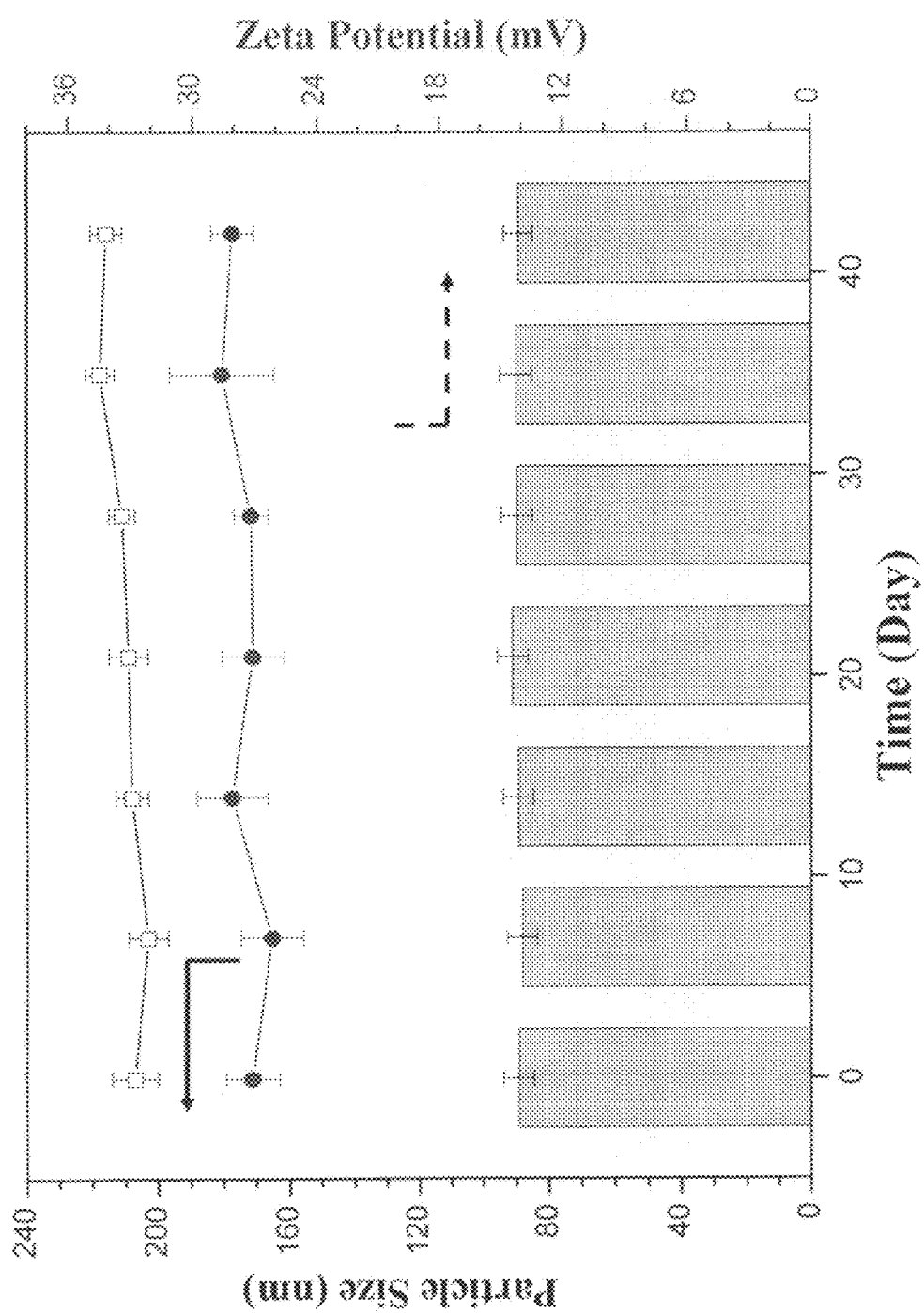
FIG. 13 shows the stability of insulin-loaded nanoparticles.

FIG. 13 shows the stability of insulin-loaded nanoparticles of the present invention with an exemplary composition of CS 0.75mg/ml, γ-PGA 0.167 mg/ml, and insulin 0.083 mg/ml. The prepared insulin-loaded nanoparticles suspended in deionized water are stable during storage up to 40 days. First (in FIG. 13), the insulin content in the nanoparticle storage solution maintains at about a constant level of 9.5%. The nanoparticle stability is further evidenced by the substantially constant particle size at about 200 nm and substantially constant zeta potential of about +28 mV over the period of about 40 days. It is contemplated that the insulin-containing nanoparticles of the present invention would further maintain their biostability when formulated in a soft gelcap configuration that further isolates the nanoparticles from environmental effects, such as sunlight, heat, air conditions, and the like. Some aspects of the invention provide a gelcap pill containing a dosage of insulin nanoparticles effective amount of the insulin to treat or manage the diabetic patients, wherein the stability of the insulin-containing nanoparticles is at least 40 days, preferably more than 6 months, and most preferably more than a couple of years. By "effective amount of the insulin", it is meant that a sufficient amount of insulin will be present in the dose to provide for a desired therapeutic, prophylatic, or other biological effect when the compositions are administered to a host in the single dosage forms.

Thus, for convenient and effective oral administration, pharmaceutically effective amounts of the nanoparticles of this invention can be tabletted with one or more excipient, encased in capsules such as gel capsules, and suspended in a liquid solution and the like. The nanoparticles can be suspended in a deionized solution or the like for parenteral administration. The nanoparticles may be formed into a packed mass for ingestion by conventional techniques. For instance, the nanoparticles may be encapsulated as a "hard-filled capsule" or a "soft-elastic capsule" using known encapsulating procedures and materials. The encapsulating material should be highly soluble in gastric fluid so that the particles are rapidly dispersed in the stomach after the capsule is ingested. Each unit dose, whether capsule or tablet, will preferably contain nanoparticles of a suitable size and quantity that provides pharmaceutically effective amounts of the nanoparticles. The applicable shapes and sizes of soft gel capsules may include round, oval, oblong, tube or suppository shape with sizes from 0.75 mm to 80 mm or larger. The volume of the capsules can be from 0.05 cc to more than 5 cc.

EXAMPLE NO. 12

In Vitro Insulin Release Study

Figure 14:
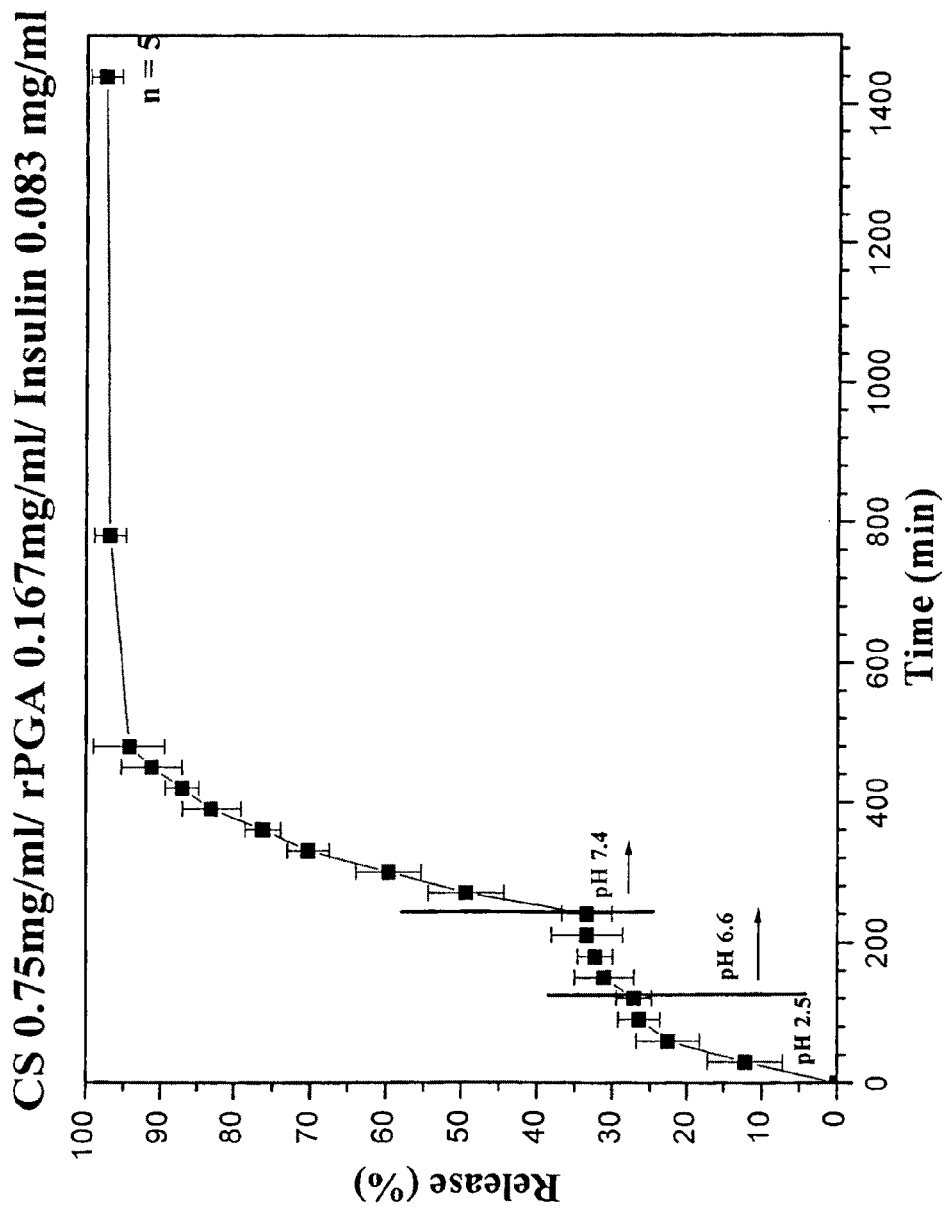
FIG. 14 shows a representative in vitro study with insulin drug release profile in a pH-adjusted solution.

FIG. 14 show a representative protein drug (for example, insulin) release profile in a pH-adjusted solution for pH-sensitivity study with an exemplary composition of CS 0.75 mg/ml, γ-PGA 0.167 mg/ml, and insulin 0.083 mg/ml in nanoparticles. In one embodiment, the exemplary composition may include each component at a concentration range of ±10% as follows: CS 0.75 mg/ml (a concentration range of 0.67 to 0.83 mg/ml), γ-PGA 0.167 mg/ml (a concentration range of 0.150 to 0.184 mg/ml), and insulin 0.083 mg/ml (a concentration range of 0.075 to 0.091 mg/ml). First, solution of the insulin-loaded nanoparticles was adjusted to pH 2.5 to simulate the gastric environment in a DISTEK-2230A container at 37° C. and 100 rpm. Samples (n=5) were taken at a pre-determined particular time interval and the particle-free solution was obtained by centrifuging at 22,000 rpm for 30 minutes to analyze the free or released insulin in solution by HPLC.

Until the free insulin content in the sample solution approaches about constant of 26% (shown in FIG. 14), the pH was adjusted to 6.6 to simulate the entrance portion of the intestine. The net released insulin during this particular time interval is about (from 26% to 33%) 7%. In other words, the nanoparticles are quite stable (evidenced by minimal measurable insulin in solution) for both the pH 2.5 and pH 6.6 regions. To further simulate the exit portion of the intestine, the insulin-containing nanoparticle solution is adjusted to pH 7.4. The remaining insulin (about 67%) is released from the nanoparticles. As discussed above, the insulin in nanoparticles would be more effective to penetrate the intestine wall in paracellular transport mode than the free insulin because of the nanoparticles of the present invention with chitosan at the outer surface (preferential mucosal adhesion on the intestinal wall) and positive charge (enhancing paracellular tight junction transport).

EXAMPLE NO. 13

In Vivo Study with Insulin-loaded Fluorescence-labeled Nanoparticles

In the in vivo study, rats were injected with streptozotocin (STZ 75 mg/kg intraperitoneal) in 0.01M citrate buffer (pH 4.3) to induce diabetes rats. The blood from the rat's tail was analyzed with a commercially available glucometer for blood glucose. The blood glucose level on Wistar male rats at no fasting (n=5) is measured at 107.2±8.1 mg/dL for normal rats while the blood glucose level is at 469.7±34.2 mg/dL for diabetic rats. In the animal study, diabetic rats were fasting for 12 hours and subjected to four different conditions: (a) oral deionized water (DI) administration; (b) oral insulin administration at 30 U/kg; (c) oral insulin-loaded nanoparticles administration at 30 U/kg; and (d) subcutaneous (SC) insulin injection at 5 U/kg as positive control. The blood glucose concentration from rat's tail was measured over the time in the study.

Figure 15:
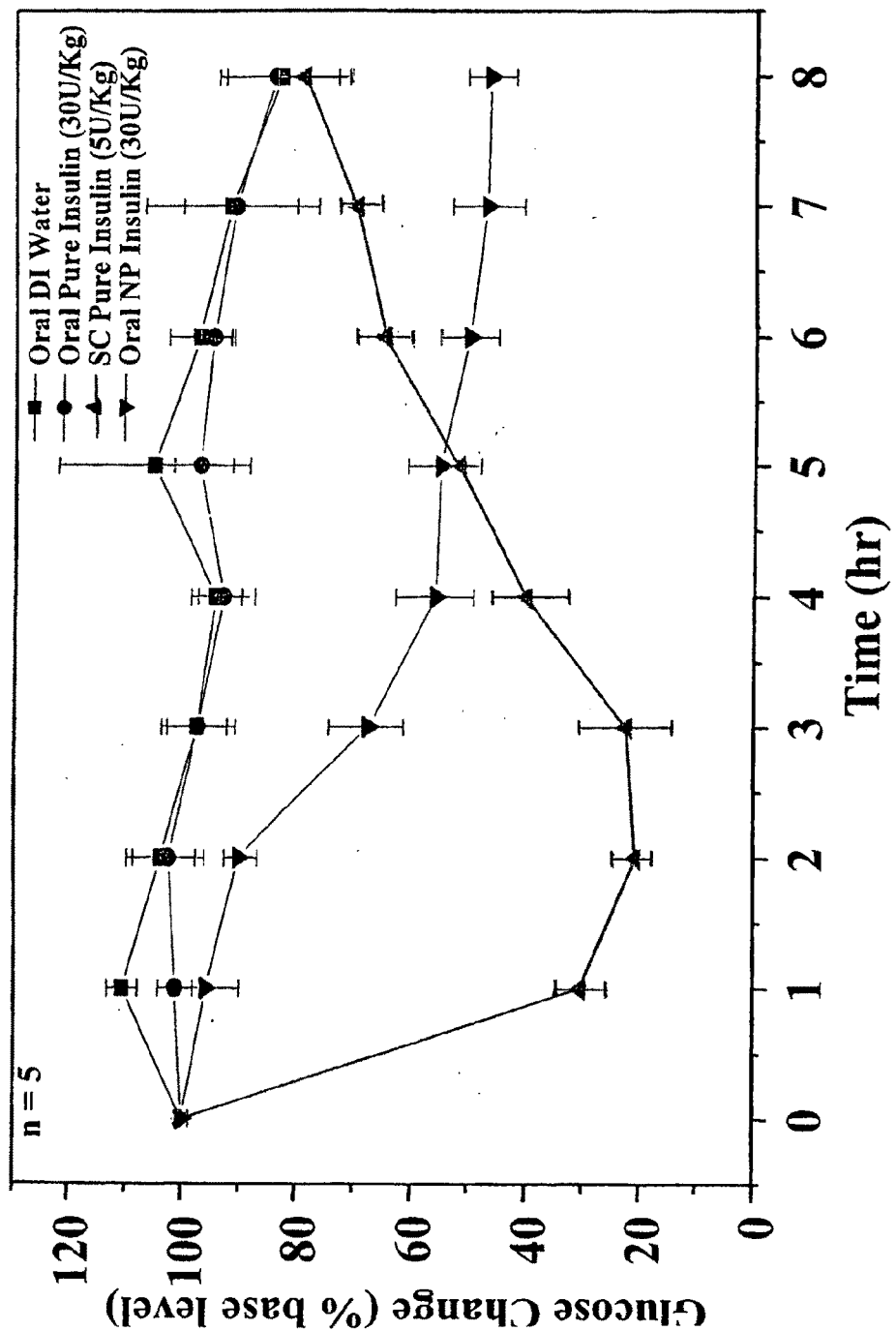
FIG. 15 shows the bioavailability of insulin of orally administered insulin-loaded nanoparticles in diabetic rats.

FIG. 15 shows glucose change (hypoglycemic index) versus time of the in vivo animal study (n=5). The glucose change as a percentage of base lines for both oral DI administration and oral insulin administration over a time interval of 8 hours appears relatively constant within the experimental measurement error range. It is illustrative that substantially all insulin from the oral administration route has been decomposed in rat stomach. As anticipated, the glucose decrease for the SC insulin injection route appears in rat blood in the very early time interval and starts to taper off after 3 hours in this exemplary study.

The most important observation of the study comes from the oral administration route with insulin-loaded nanoparticles. The blood glucose begins to decrease from the base line at about 2 hours after administration and sustains at a lower glucose level at more than 8 hours into study. It implies that the current insulin-loaded nanoparticles may modulate the glucose level in animals in a sustained or prolonged effective mode. Some aspects of the invention provide a method of treating diabetes of a patient comprising orally administering insulin-containing nanoparticles with a dosage effective amount of the insulin to treat the diabetes, wherein at least a portion of the nanoparticles comprises a positively charged shell substrate and a negatively charged core substrate. In one embodiment, the dosage effective amount of the insulin to treat the diabetes comprises an insulin amount of between about 15 units to 45 units per kilogram body weight of the patient, preferably 20 to 40 units, and most preferably at about 25 to 35 units insulin per kilogram body weight.

Some aspects of the invention relate to a novel nanoparticle system that is composed of a low-MW CS and γ-PGA with CS dominated on the surfaces being configured to effectively open the tight junctions between Caco-2 cell monolayers. The surface of the nanoparticles is characterized with a positive surface charge. In one embodiment, the nanoparticles of the invention enables effective intestinal delivery for bioactive agent, including peptide, polypeptide, protein drugs, other large hydrophilic molecules, and the like. Such polypeptide drugs can be any natural or synthetic polypeptide that may be orally administered to a human patient.

Exemplary drugs of the present invention include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors: interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; vaccines; monoclonal antibodies; and the like; and analogs and derivatives of these compounds.

The bioactive agent of the present invention may be selected from group consisting of oxytocin, vasopressin, adrenocorticotrophic hormone, prolactin, luliberin or luteinising hormone releasing hormone, growth hormone, growth hormone releasing factor, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines.

In another embodiment, the nanoparticles of the invention increase the absorption of bioactive agents across the blood brain barrier and/or the gastrointestinal barrier. In still another embodiment, the nanoparticles with chitosan at an outer layer and surface positive charge serve as an enhancer in enhancing paracellular drug (bioactive agent) transport of an administered bioactive agent when the bioactive agent and nanoparticles are orally administrated in a two-component system, or orally administered substantially simultaneously.

EXAMPLE NO. 14

Paracelular Transport and Enhancers

Chitosan and its derivatives may function as intestinal absorption enhancers (that is, paracellular transport enhancers). Chitosan, when protonated at an acidic pH, is able to increase the paracellular permeability of peptide drugs across mucosal epithelia. Some aspects of the invention provide co-administration of nanoparticles of the present invention and at least one paracellular transport enhancer (in non-nanoparticle form or nanoparticle form). In one embodiment, the nanoparticles can be formulated by co-encapsulation of the at least one paracellular transport enhancer and at least one bioactive agent, optionally with other components. The enhancer may be selected from the group consisting of $Ca^{2+}$ chelators, bile salts, anionic surfactants, medium-chain fatty acids, phosphate esters, and chitosan or chitosan derivatives. In one embodiment, the nanoparticles of the present invention comprises a positively charged shell substrate and a negatively charged core substrate, for example, nanoparticles composed of γ-PGA and chitosan that is characterized with a substantially positive surface charge.

In some embodiment, the nanoparticles of the present invention and the at least one paracellular transport enhancer are encapsulated in a soft gel, pill, or enteric coated. The enhancers and the nanoparticles would arrive at the tight junction about the same time for enhancing opening the tight junction. In another embodiment, the at least one paracellular transport enhancer is co-enclosed within the shell of the nanoparticles of the present invention. Therefore, some broken nanoparticles would release enhancers to assist the nanoparticles to open the tight junctions of the epithelial layers. In an alternate embodiment, the at least one enhancer is enclosed within a second nanoparticle having positive surface charges, particularly a chitosan type nanoparticle. When the drug-containing first nanoparticles of the present invention are co-administered with the above-identified second nanoparticles orally, the enhancers within the second nanoparticles are released in the intestinal tract to assist the drug-containing first nanoparticles to open and pass the tight junction.

EXAMPLE NO. 15

Nanoparticles with Complexed Calcitonin

Calcitonin is a protein drug that serves therapeutically as calcium regulators for treating osteoporosis (J. Pharm. Pharmacol. 1994;46:547-552). Calcitonin has a molecular formula of $C_{145}H_{240}N_{44}O_{48}S_2$ with a molecular weight of about 3431.9 and an isoelectric point of 8.7. The net charge for calcitonin at pH7.4 is positive that is suitable to complex or conjugate with negatively charged core substrate, such as γ-PGA or α-PGA. In preparation, nanoparticles were obtained upon addition of a mixture of γ-PGA plus calcitonin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at concentrations higher than 0.10% by w/v under magnetic stirring at room temperature to ensure positive surface charge. Nanoparticles were collected by ultracentrifugation at 38,000 rpm for 1 hour. Calcitonin is totally or substantially totally encapsulated in the nanoparticles. Supernatants were discarded and nanoparticles were resuspended in deionized water as the solution products, further encapsulated in soft gels or further treated with an enteric coating.

Preotact® (parathyroid hormone) has been demonstrated to increase bone size and mineral content, thereby improving bone quality and strength. These biological actions are mediated through binding to at least two distinct high-affinity cell-surface receptors specific for the N-terminal and C-terminal regions of the molecule, both of which are required for normal bone metabolism. The N-terminal portion of the molecule is primarily responsible for the bone building effects of parathyroid hormone. The C-terminal portion of the molecule has antiresorptive activity and is necessary for normal regulation of N-terminal fragment activity. The normal physiological role of parathyroid hormone (rDNA origin) is to regulate calcium and phosphate homeostasis. Actions of parathyroid hormone include regulation of bone metabolism, renal tubular reabsorption by stimulating the renal production of the active metabolite of vitamin D. Preotact® is injected with the specially designed and patient focused Preotact™ Pen.

Parathyroid hormone (PTH) is secreted by the parathyroid glands as a polypeptide containing 84 amino acids. It acts to increase the concentration of calcium in the blood, whereas calcitonin (a hormone produced by the thyroid gland) acts to decrease calcium concentration. PTH acts to increase the concentration of calcium in the blood in three ways. It enhances the release of calcium from the large reservoir contained in the bones, enhances reabsorption of calcium from renal tubules; and enhances the absorption of calcium in the intestine by increasing the production of vitamin D and upregulating the enzyme responsible for 1-alpha hydroxylation of 25-OH vitamin D converting vitamin D to its active form (1.25-OH vitamin D) which effects the actual absorption of calcium by the intestine.

PTH also acts to decrease the concentration of phosphate in the blood, primarily by reducing reabsorption in the proximal tubules of the kidney. Increased calcium concentration in the blood acts (via feedback inhibition) to decrease PTH secretion by the parathyroid glands. This is achieved by the activation of calcium-sensing receptors located on parathyroid cells. Preotact(® (or Preos®, a U.S. version) is recombinant full-length human parathyroid hormone (PTH 1-84).

Some aspects of the invention relate to a pharmaceutical composition of nanoparticles for oral administration in a patient, comprising a biodegradable chitosan shell substrate, and a parathyroid hormone encapsulated within the shell substrate. In one embodiment, the parathyroid hormone is polypeptide containing 84 amino acids that is recombinant full-length human parathyroid hormone (PTH 1-84).

Erythropoietin

Erythropoietin (EPO) is a hormone that is a cytokine for erythrocyte (red blood cell) precursors in the bone marrow. It is produced by the kidney, and is the hormone regulating red blood cell production. After being released into the blood stream it binds with receptors (EpoR) on the surface or red cell precursors in the bone marrow, where it stimulates the production of red blood cells. Synthetic erythropoietin is available as a therapeutic agent produced by recombinant DNA technology (rEPO). It is used in treating anemia resulting from chronic renal failure or from cancer chemotherapy. EPO has now been identified as a glycoprotein with a molecular mass of about 30,000 Daltons. It has a 165 amino acid chain with four oligosaccharide side chains and circulates in the blood plasma at a very low concentration (about 5 pmol/L). Erythropoietin, an acidic glycoprotein of approximately 34,000 molecular weight, may occur in three forms: α, β, and asialo. The α and β forms differ slightly in carbohydrate components, but have the same potency, biological activity and molecular weight. The asialo form is an α or β form with the terminal carbohydrate (sialic acid) removed.

A longer-acting erythropoietin analogue, darbepoetin (dEPO), also known as novel erythropoiesis-stimulating protein (NESP), has a slightly different amino acid sequence and a greater number of oligosaccharide residues, relative to rEPO. EPO is generally injected subcutaneously (under the skin) by the patient, although it may also be given intravenously. Some aspects of the invention relate to a pharmaceutical composition of nanoparticles for oral administration in a patient, comprising a biodegradable chitosan shell substrate, and a rEPO or dEPO encapsulated within the shell substrate, wherein the rEPO or dEPO is sustained released into blood circulation via intestinal paracellular permeation.

EXAMPLE NO. 16

Nanoparticles With Encapsulated Erythropoietin

In product formulation, nanoparticles were obtained upon addition of erythropoietin (in one example for illustration, rEPO) aqueous solution, using a pipette into a low-MW CS aqueous solution with excess CS concentrations under magnetic stirring at room temperature. Nanoparticles were collected by ultracentrifugation. Nanoparticles comprise positively charged shell substrate chitosan and negatively charged core substrate erythropoietin. The erythropoietin is substantially or totally encapsulated in the nanoparticles. In other words, the erythropoietin component is substantially maintained within the intact nanoparticles during the nanoparticle delivery phase orally. Thus, erythropoietin does not cause any significant effect until the nanoparticles dissociate or biodegrade to release the core contents in a sustained release manner into the blood stream.

EXAMPLE NO. 17

Nanoparticles Loaded With Vancomycin

Vancomycin is a protein drug that serves therapeutically as antibiotic against bacterial pathogens. Vancomycin has a molecular formula of $C_{66}H_{75}N_9O_{24}$ with a molecular weight of about 1485.7 and an isoelectric point of 5.0. The net charge for vancomycin at pH7.4 is negative that is suitable to complex or conjugate with a portion of negatively charged shell substrate, such as chitosan. In preparation, nanoparticles were obtained upon addition of a mixture of γ-PGA plus vancomycin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature, wherein CS concentration is provided sufficiently to conjugate vancomycin, to counterbalance γ-PGA, and exhibit positive surface charge for the nanoparticles. Nanoparticles were collected by ultracentrifugation at 38,000 rpm for 1 hour. Vancomycin is wholly or substantially totally encapsulated in the nanoparticles. Supernatants were discarded and nanoparticles were resuspended in deionized water as the solution products, further encapsulated in soft gels or further treated with an enteric coating.

Some aspects of the invention relate to a method of enhancing intestinal or blood brain paracellular transport of bioactive agents configured and adapted for delivering at least one bioactive agent in a patient comprising administering nanoparticles composed of γ-PGA and chitosan, wherein the nanoparticles are loaded with a therapeutically effective amount or dose of the at least one bioactive agent. The nanoparticle of the present invention is an effective intestinal delivery system for peptide and protein drugs and other large hydrophilic molecules. In a further embodiment, the bioactive agent is selected from the group consisting of proteins, peptides, nucleosides, nucleotides, antiviral agents, antineoplastic agents, antibiotics, and anti-inflammatory drugs. In a further embodiment, the bioactive agent is selected from the group consisting of calcitonin, cyclosporin, insulin, oxytocin, tyrosine, enkephalin, tyrotropin releasing hormone (TRH), follicle stimulating hormone (FSH), luteinizing hormone (LH), vasopressin and vasopressin analogs, catalase, superoxide di smutase, interleukin-II (IL2), interferon, colony stimulating factor (CSF), tumor necrosis factor (TNF) and melanocyte-stimulating hormone. In a further embodiment, the bioactive agent is an Alzheimer antagonist.

EXAMPLE NO. 18

Nanoparticles with Heparin Core Substrate

Heparin is a negatively charged drug that serves therapeutically as anti-coagulant. Heparin is generally administered by intravenous injection. Some aspects of the invention relate to heparin nanoparticles for oral administration or subcutaneous administration. In a further embodiment, heparin serves as at least a portion of the core substrate with chitosan as shell substrate, wherein heparin conjugate at least one bioactive agent as disclosed herein. In preparation, nanoparticles were obtained upon addition of heparin Leo aqueous solution (2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature. Nanoparticles were collected by ultracentrifugation at 38,000 rpm for 1 hour. Heparin is totally or substantially totally encapsulated in the nanoparticles. In other words, heparin is substantially maintained within the intact nanoparticles during the nanoparticle delivery phase orally. Thus, heparin does not cause any significant effect until the nanoparticles dissociate or biodegrade to release the core contents. Table 4 shows the conditions of solution preparation and the average nanoparticle size.

TABLE 4

| Conditions | Heparin conc. @2 ml | Chitosan conc. @10 ml | Particle size (nm) |
|---|---|---|---|
| A | 200 iu/ml | 0.09% | 298.2 ± 9.3 |
| B | 100 iu/ml | 0.09% | 229.1 ± 4.5 |
| C | 50 iu/ml | 0.09% | 168.6 ± 1.7 |
| D | 25 iu/ml | 0.09% | 140.1 ± 2.3 |

To evaluate the pH stability of the heparin-containing nanoparticles from Example no. 17, the nanoparticles from Condition D in Table 4 are subjected to various pH for 2 hours (sample size=7). Table 5 shows the average size, size distribution (polydispersity index: PI) and zeta potential (Zeta) of the nanoparticles at the end of 2 hours under various pH environments. The data shows the nanoparticles are relatively stable. In one embodiment, the nanoparticles of the present invention may include heparin, heparin sulfate, small molecular weight heparin, and heparin derivatives.

TABLE 5

| pH | 1.5 | 2.6 | 6.6 | 7.4 | Deionized water @5.9 |
|---|---|---|---|---|---|
| Size (nm) | 150 ± 9 | 160 ± 12 | 153 ± 2 | 154 ± 4 | 147 ± 5 |
| PI | 0.54 ± 0.03 | 0.50 ± 0.04 | 0.08 ± 0.02 | 0.32 ± 0.03 | 0.37 ± 0.02 |
| Zeta(+) | 15 ± 2 | 33 ± 6 | 15 ± 0.1 | 11 ± 0.2 | 18 ± 4 |

In a further embodiment, a growth factor such as bFGF with pharmaceutically effective amount is added to heparin Leo aqueous solution before the pipetting step in Example No. 16. In our laboratory, growth factors and proteins with pharmaceutically effective amount have been successfully conjugated with heparin to form nanoparticles of the present invention with chitosan as the shell substrate, wherein the growth factor is selected from the group consisting of Vascular Endothelial Growth Factor (VEGF), Vascular Endothelial Growth Factor 2 (VEGF2), basic Fibroblast Growth Factor (bFGF), Vascular Endothelial Growth Factor 121 (VEGF121), Vascular Endothelial Growth Factor 165 (VEGF165), Vascular Endothelial Growth Factor 189 (VEGF 189), Vascular Endothelial Growth Factor 206 (VEGF206), Platelet Derived Growth Factor (PDGF), Platelet Derived Angiogenesis Factor (PDAF), Transforming Growth Factor-β (TGF-β), Transforming Growth Factor-α (TGF-α), Platelet Derived Epidermal Growth Factor (PDEGF), Platelet Derived Wound Healing Formula (PDWHF), epidermal growth factor, insulin-like growth factor, acidic Fibroblast Growth Factor (aFGF), human growth factor, and combinations thereof, and the protein is selected from the group consisting of haemagglutinin (HBHA), Pleiotrophin, buffalo seminal plasma proteins, and combinations thereof.

In a co-pending application, U.S. patent application Ser. No. 10/916,170 filed Aug. 11, 2004, it is disclosed that a biomaterial with free amino groups of lysine, hydroxylysine, or arginine residues within biologic tissues is crosslinkable with genipin, a crosslinker (Biomaterials 1999;20:1759-72). It is also disclosed that the crosslinkable biomaterial may be crosslinked with a crosslinking agent or with light, such as ultraviolet irradiation, wherein the crosslinkable biomaterial may be selected from the group consisting of collagen, gelatin, elastin, chitosan, NOCC (N, O, carboxylmethyl chitosan), fibrin glue, biological sealant, and the like. Further, it is disclosed that a crosslinking agent may be selected from the group consisting of genipin, its derivatives, analog (for example, aglycon geniposidic acid), stereoisomers and mixtures thereof. In one embodiment, the crosslinking agent may further be selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers, and the like.

In one embodiment, it is disclosed that loading drug onto a chitosan-containing biological material crosslinked with genipin or other crosslinking agent may be used as biocompatible drug carriers for drug slow-release or sustained release. Several biocompatible plastic polymers or synthetic polymers have one or more amine group in their chemical structures, for example poly(amides) or poly(ester amides). The amine group may become reactive toward a crosslinking agent, such as glutaraldehyde, genipin or epoxy compounds of the present invention. In one embodiment, the nanoparticles comprised of crosslinkable biomaterial is crosslinked, for example up to about 50% degree or more of crosslinking, preferably about 1 to about 20% degree of crosslinking of the crosslinkable components of the biomaterial, enabling sustained biodegradation of the biomaterial and/or sustained drug release.

By modifying the chitosan structure to alter its charge characteristics, such as grafting the chitosan with methyl, alkyl (for example, ethyl, propyl, butyl, isobutyl, etc.), polyethylene glycol (PEG), or heparin (including low molecular weight heparin, regular molecular weight heparin, and genetically modified heparin), the surface charge density (zeta potential) of the CS-γ PGA nanoparticles may become more pH resistant or hydrophilic. In one embodiment, the chitosan is grafted with polyacrylic acid or a polymer with a chemical formula:

$$O=C\begin{smallmatrix}\diagup NH\\ \diagdown\kern-0.5em\diagdown\\ R\end{smallmatrix}$$

where R is ≥ 12

By way of illustration, trimethyl chitosan chloride might be used in formulating the CS-γ PGA nanoparticles for maintaining its spherical biostability at a pH lower than pH 2.5, preferably at a pH as low as 1.0. Some aspects of the invention provide a drug-loaded chitosan-containing biological material crosslinked with genipin or other crosslinking agent as a biocompatible drug carrier for enhancing biostability at a pH lower than pH 2.5, preferably within at a pH as low as 1.0.

Figure 16:
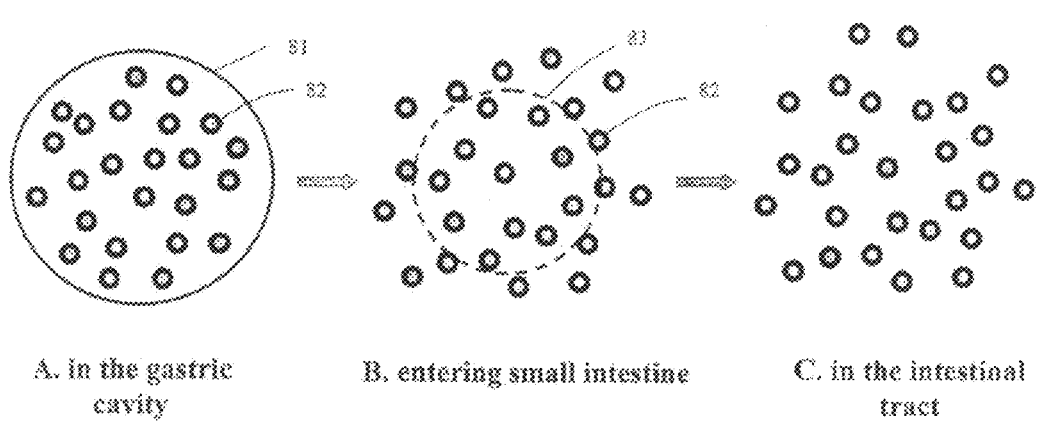
FIG. 16 shows a proposed mechanism of nanoparticles released from the enteric coating.

FIG. 16 shows an illustrative mechanism of nanoparticles released from the enteric coating. FIG. 16(A) shows the phase of nanoparticles in the gastric cavity, wherein the nanoparticles 82 are encapsulated within an initial enteric coating 81. FIG. 16(B) shows a schematic of the coated nanoparticles during the phase of entering small intestine, wherein the enteric coating starts to dissolve 83 and a portion of nanoparticles 83 starts to release. FIG. 16(C) shows the phase of nanoparticles in the intestinal tract, wherein the nanoparticles open the tight junctions as described above. In an alternate embodiment, nanoparticles may be released from alginate-calcium coating. In preparation, nanoparticles are first suspended in a solution that contains calcium chloride, wherein the calcium ions are positively charged. With a pipette, alginate with negatively charged carboxyl groups is slowly added to the calcium chloride solution. Under gentle stirring, the alginate-calcium starts to conjugate, gel, and coat on the nanoparticle surface. In simulated oral administration of the alginate-calcium coated nanoparticles, nanoparticles start to separate from the coating when they enter the small intestines.

Figure 17:
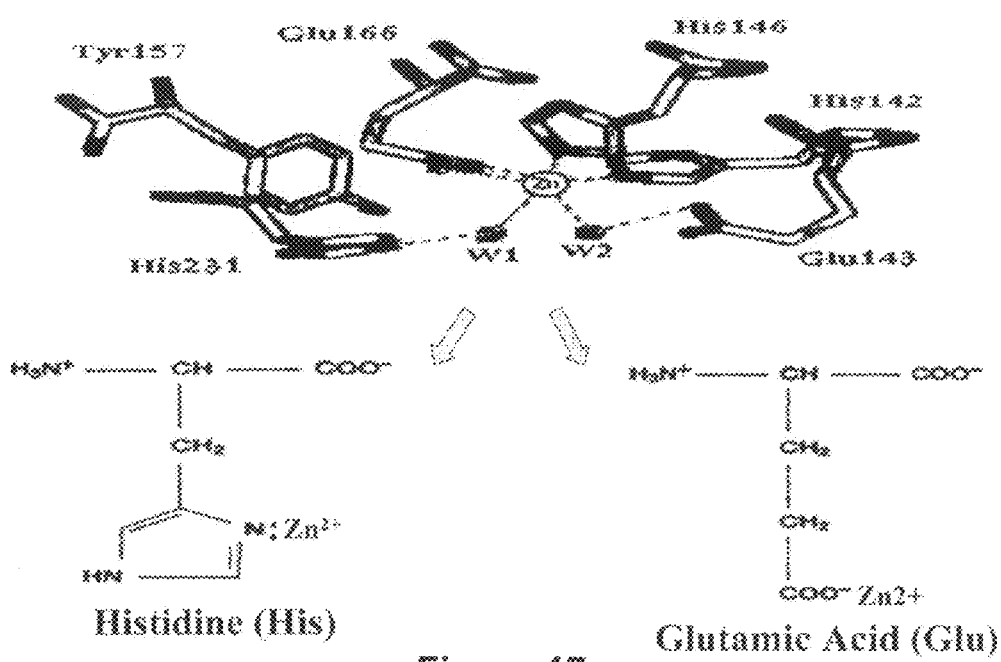
FIG. 17 shows the schematic illustration of insulin conjugated with histidine and/or glutamic acid side groups of the γ-PGA via zinc.
Figure 18:
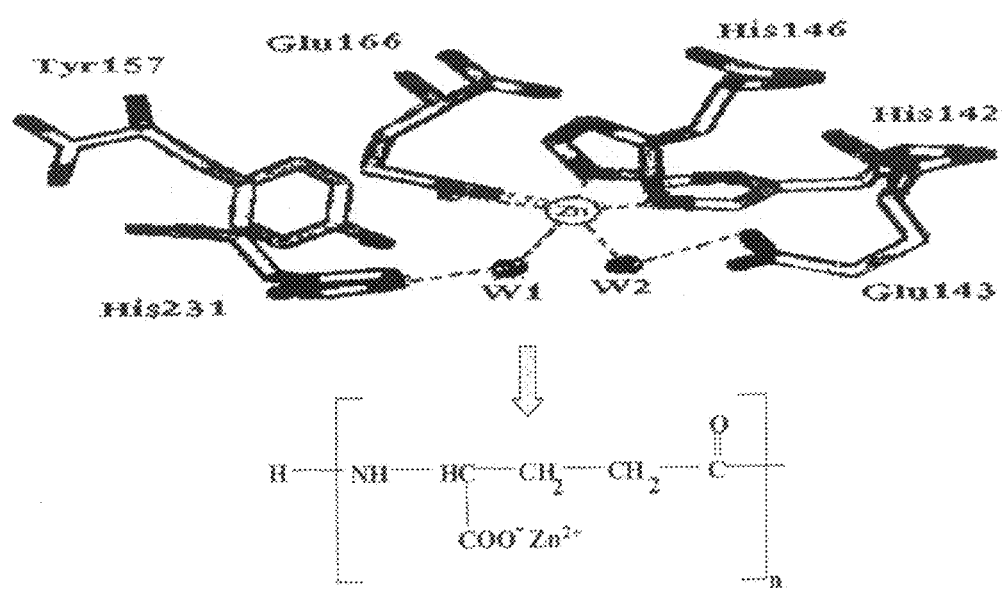
FIG. 18 shows the schematic illustration of insulin conjugated with a carboxyl side group of the γ-PGA via zinc.

It is known that Zn (zinc) is usually added in the biosynthesis and storage of insulin. FIGS. 17 and 18 show a schematic of insulin conjugated with a polyanionic compound (i.e., γ-PGA in this case) via Zn and thus increase its loading efficiency and loading content in the nanoparticles of the present invention. It is further demonstrated that Zn may complex with the histidine and glutamic acid residues in insulin to increase the insulin stability and enhance controlled release capability or sustained therapy. Some aspects of the invention relate to a nanoparticle characterized by enhancing intestinal or brain blood paracellular transport, the nanoparticle comprising a first component of at least one bioactive agent, a second component of low molecular weight chitosan, and a third component that is negatively charged, wherein a stabilizer is added to complex the at least one bioactive agent to the negatively charged third component. In one embodiment, the stabilizer is zinc or calcium.

One aspect describes a nanoparticle system encapsulating abatacept for oral administration via intestinal absorption routes. Orencia® (Abatacept) is an injectable, synthetic (man-made) protein produced by recombinant DNA technology that is used for treating rheumatoid arthritis. T-lymphocytes are important cells of the immune system. Patients with rheumatoid arthritis have increased numbers of T-lymphocytes within the joints that are inflamed. The T-lymphocytes are activated, that is, they multiply and release chemicals that promote the destruction of tissues surrounding the joints and cause the signs and symptoms of rheumatoid arthritis. Abatacept acts like an antibody and attaches to a protein on the surface of T-lymphocytes. By attaching to the protein, abatacept prevents the activation of the T-lymphocytes and blocks both the production of new T-lymphocytes and the production of the chemicals that destroy tissue and cause the symptoms and signs of arthritis. Abatacept slows the damage to bones and cartilage and relieves the symptoms and signs of arthritis. Abatacept was approved by the FDA in December 2005. As typical with injection, Abatacept is infused over 30 minutes. The initial dose of abatacept is followed by a second dose two weeks later with further doses every 4 weeks thereafter.

Monoclonal Antibody

Substances foreign to the body, such as disease-causing bacteria and viruses and other infectious agents, known as antigens, are recognized by the body's immune system as invaders. Our natural defenses against these infectious agents are antibodies, proteins that seek out the antigens and help destroy them. Immunoglobulins are glycoproteins in the immunoglobulin superfamily that function as antibodies. The terms antibody and immunoglobulin are often used interchangeably. They are found in the blood and tissue fluids, as well as many secretions. In structure, they are globulins (in the $\gamma$-region of protein electrophoresis). They are synthesized and secreted by plasma cells that are derived from the B cells of the immune system. B cells are activated upon binding to their specific antigen and. differentiate into plasma cells. In some cases, the interaction of the B cell with a T helper cell is also necessary. The nominal size of an antibody is about 10 nm.

Humans have the ability to make antibodies able to recognize (by binding to) virtually any antigenic determinant (i.e., epitope) and to discriminate between even similar epitopes. An epitope is a small piece of the antigen to which the antibody binds. Not only does this provide the basis for protection against disease organisms, but also it makes antibodies attractive candidates to target other types of molecules found in the body, such as receptors or other proteins present on the surface of normal cells and molecules present uniquely on the surface of cancer cells. Thus the remarkable specificity of antibodies makes them promising agents for human therapy. It has been suggested to make an antibody that will bind only to the cancer cells in a patient, couple a cytotoxic agent (e.g. a strong radioactive isotope or cancer-killing paclitaxel) to that antibody, and then give the complex to the patient so it can seek out and destroy the cancer cells (and no normal cells).

Monoclonal antibodies are widely used as diagnostic and research reagents. Their introduction into human therapy has been much slower. Reimbursement of self-administered biologics, particularly the oral administration route, under Medicare Part D will significantly improve access to biologics and expand the market. In some in vivo applications, the antibody itself is sufficient. Once bound to its target, it triggers the normal effector mechanisms of the body, such as alerting other cells in the immune system to the presence of the cancer cells. In other cases, the monoclonal antibody is coupled to another molecule, for example a fluorescent molecule to aid in imaging the target or a strongly-radioactive atom, such as Iodine-131 to aid in killing the target.

Some monoclonal antibodies that have been introduced into human medicine include those that suppress the immune system, such as:

Muromonab-CD3 (OKT3) and two humanized anti-CD3 monoclonals. Bind to the CD3 molecule on the surface of T cells. Used to prevent acute rejection of organ, e.g., kidney transplants. The humanized versions show promise in inhibiting the autoimmune destruction of beta cells in Type 1 diabetes mellitus.

Infliximab (Remicade®). Binds to tumor necrosis factor-alpha (TNF-$\alpha$). Shows promise against some inflammatory diseases such as rheumatoid arthritis.

Omalizumab (Xolair®). Binds to IgE thus preventing IgE from binding to mast cells. Shows promise against allergic asthma.

Daclizumab (Zenapax®). Binds to part of the IL-2 receptor produced at the surface of activated T cells. Used to prevent acute rejection of transplanted kidneys. Has also showed promise against T-cell lymphoma.

Some monoclonal antibodies that have been introduced into human medicine include those that kill or inhibit malignant cells, such as:

Rituximab (Rituxan®). Binds to the CD20 molecule found on most B-cells and is used to treat B-cell lymphomas. It shows efficacy for treating the patient population that is refractory to treatment (either do not respond to therapy or cannot tolerate therapy) with TNF inhibitors, such as Adalimumab.

Zevalin®. This is a monoclonal antibody against the CD20 molecule on B cells (and lymphomas) conjugated to either the radioactive isotope indium-111 ($^{111}$In) or the radioactive isotope yttrium-90 ($^{90}$Y)

Bexxar® (tositumomab). This is a conjugate of a monoclonal antibody against CD20 and the radioactive isotope iodine-131 ($^{131}$I). It is designed as a treatment for lymphoma.

Herceptin® (trastuzumab). Binds HER2, a receptor for epidermal growth factor (EGF) that is found on some tumor cells (some breast cancers, lymphomas). The only monoclonal so far that seems to be effective against solid tumors.

Erbitux® (cetuximab). Blocks HERl, another epidermal growth factor (EGF) receptor.

Mylotarg®. A conjugate of a monoclonal antibody that binds CD33, a cell-surface molecule expressed by the cancerous cells in acute myelogenous leukemia (AML) but not found on the normal stem cells needed to repopulate the bone marrow. calicheamicin, a complex oligosaccharide that makes double-stranded breaks in DNA. Mylotarg® is the first immunotoxin that shows promise in the fight against cancer.

LymphoCide. Binds to CD22, a molecule found on some B-cell leukemias.

Alemtuzumab (MabCampath®). Binds to CD52, a molecule found on white blood cells. Has produced complete remission of chronic lymphocytic leukemia.

Certolizumab pegol CDP870 (Cimzia®). Cimzia is the first and only PEGylated Fab' fragment of a humanized anti-TNF alpha antibody. The engineered Fab' fragment retains the biologic potency of the original antibody. Cimzia has a high affinity for human TNF alpha, selectively neutralizing the pathophysiological effects of TNF alpha. Over the past decade, TNF has emerged as a major target of basic research and clinical investigation. This cytokine plays a key role in mediating pathological inflammation, and excess TNF production has been directly implicated in a wide variety of diseases.

Lym-1 (Oncolym®). Binds to the HLA-DR-encoded histocompatibility antigen that can be expressed at high levels on lymphoma cells.

Some monoclonal antibodies that have been introduced into human medicine include those that inhibit angiogenesis or perform other function, such as:

Vitaxin. Binds to a vascular integrin (alpha-v/beta-3) found on the blood vessels of tumors but not on the blood vessels supplying normal tissues. In Phase II clinical trials, Vitaxin has shown some promise in shrinking solid tumors without harmful side effects.

Bevacizumab (Avastin®). Binds to vascular endothelial growth factor (VEGF) preventing it from binding to its receptor. Approved by the US FDA in February 2004 for the treatment of colorectal cancers.

Abciximab (ReoPro®). Inhibits the clumping of platelets by binding the receptors on their surface that normally are linked by fibrinogen. Helpful in preventing reclogging of the coronary arteries in patients who have undergone angioplasty.

In additional to the above monoclonal antibodies, other approved monoclonal antibodies may include, but not limited to, Basiliximab, Gemtuzumab ozogamicin, Ibritumomab, Palivizumab, Eculizumab, Adalimumab (Humira®), and Efalizumab.

By way of illustration, Natalizumab is a monoclonal antibody bioengineered from part of a mouse antibody to closely resemble a human antibody. It is being marketed under the trade name Tysabri®. The product is given intravenously once a month in a physician's office for treating multiple sclerosis (MS) to reduce the frequency of symptom flare-ups or exacerbations of the disease. MS is a chronic, often disabling disease of the brain and spinal cord.

By way of illustration, Rituximab targets a protein called CD20, found on the surface of type B lymphocytes. These are one of the main types of white blood cells, and the cell at fault in most cases of non-Hodgkin's lymphoma. Although the drug attacks both cancerous and non-cancerous type B cells, the body quickly replaces them with healthy lymphocytes. Monoclonal antibodies have been designed to recognize certain proteins found on the surface of some cancer cells. Once the monoclonal antibody has recognized the protein, it locks on to it and triggers the body's immune system to attack the cancer cells, without affecting other cells in the body. Sometimes it instructs the cells to destroy themselves.

One possible treatment for cancer involves monoclonal antibodies (mAb) that bind only to cancer cell-specific antigens and induce an immunological response against the target cancer cell. Such mAb could also be modified for delivery of a toxin, radioisotope, cytokine or other active conjugate; it is also possible to design bispecific antibodies that can bind with their Fab regions both to target antigen and to a conjugate or effector cell. In fact, every intact antibody can bind to cell receptors or other proteins with its Fc region.

Antibody Structure and Binding with Antigen

Immunoglobulins are heavy plasma proteins, often with added sugar chains on N-terminal (all antibodies) and occasionally O-terminal (IgA1 and IgD) amino acid residues. According to differences in their heavy chain constant domains, immunoglobulins are grouped into five classes, or isotypes: IgG, IgA, IgM, IgD, and IgE. Other immune cells collaborate with antibodies to eliminate pathogens depending on which IgG, IgA, IgM, IgD, and IgE constant binding domain receptors it can express on its surface.

The basic unit of each antibody is a monomer. An antibody can be monomeric, dimeric, trimeric, tetrameric, pentameric, etc. The monomer is a "Y"-shape molecule that consists of two identical heavy chains and two identical light chains connected by disulfide bonds. There are five types of heavy chain: $\gamma$, $\delta$, $\alpha$, $\mu$ and $\epsilon$. They define classes of immunoglobulins. Each heavy chain has a constant region, which is the same by all immunoglobulins of the same class, and a variable region, which differs between immunoglobulins of different B cells, but is the same for all immunoglobulins produced by the same B cell. Heavy chains $\gamma$, $\alpha$ and $\delta$ have the constant region composed of three domains but have a hinge region; the constant region of heavy chains $\mu$ and $\epsilon$ is composed of four domains. The variable domain of any heavy chain is composed of one domain. These domains are about 110 amino acids long. There are also some amino acids between constant domains.

The "Y"-shaped monomer has two heavy and two light chains. Together this gives six to eight constant domains and four variable domains. Each half of the forked end of the "Y" is called an Fab fragment. It is composed of one constant and one variable domain of each the heavy and the light chain, which together shape the antigen binding site at the amino terminal end of the monomer. The two variable domains bind their specific antigens. The enzyme papain cleaves a monomer into two Fab (fragment antigen binding) fragments and an Fc (fragment crystallizable) fragment. The enzyme pepsin cleaves below hinge region, so a Fab fragment and a Fc fragment is formed. Together, the antibodies in an organism can bind a wide variety of foreign antigens.

The antibodies have two primary functions: they bind antigens and they combine with different immunoglobulin receptors specific for them and exert effector functions. These receptors are isotype-specific, which gives a great flexibility to the immune system, because different situations require only certain immune mechanisms to respond to antigens. By "Affinity" is herein defined as the binding strength of the antibody to the antigen. By "Avidity" is herein defined as the number of antigen binding sites.

Antibodies exist freely in the bloodstream or bound to cell membranes. They are part of the humoral immune system. Antibodies exist in clonal lines that are specific to only one antigen, e.g., a virus hull protein. In binding to such antigens, they can cause agglutination and precipitation of antibody-antigen products primed for phagocytosis by macrophages and other cells, block viral receptors, and stimulate other immune responses, such as the complement pathway. Antibodies that recognize viruses can block these directly by their sheer size. The virus will be unable to dock to a cell and infect it, hindered by the antibody. They can also agglutinate them so the phagocytes can capture them. Antibodies that recognize bacteria mark them for ingestion by phagocytes, a process called opsonization. Together with the plasma component complement, antibodies can kill bacteria directly. They neutralize toxins by binding with them.

In biochemistry, antibodies are used for immunological identification of proteins, using the Western blot method. A similar technique is used in ELISPOT and ELISA assays, in which detection antibodies are used to detect cell secretions such as cytokines or antibodies. Antibodies are also used to separate proteins (and anything bound to them) from the other molecules in a cell lysate. A Western blot (a.k.a immunoblot) is a method in molecular biology/biochemistry/immunogenetics to detect protein in a given sample of tissue homogenate or extract. It uses gel electrophoresis to separate denatured proteins by mass. The proteins are then transferred out of the gel and onto a membrane (typically nitrocellulose), where they are "probed" using antibodies specific to the protein. As a result, researchers can examine the amount of protein in a given sample and compare levels between several groups.

The Enzyme-Linked ImmunoSorbent Assay (ELISA for short) is a biochemical technique used mainly in immunology to detect the presence of an antibody or an antigen in a sample. It utilizes two antibodies, one of which is specific to the antigen and the other of which is coupled to an enzyme. This second antibody gives the assay its "enzyme-linked" name, and will cause a chromogenic or fluorogenic substrate to produce a signal. Because the ELISA can be performed to evaluate either the presence of antigen or the presence of antibody in a sample, it is a useful tool both for determining serum antibody concentrations (such as with the Human Immunodeficiency Virus, HIV test or West Nile Virus) and also for detecting the presence of antigen. ELISPOT is an immunological assay based on ELISA. Basically, the difference between the two is that in ELISA, the substance containing the "unknown" is stuck at the bottom of the well, whereas in ELISPOT the substance with the "unknown" is placed in the well after the bottom of the well has been coated with cytokine-specific antibody. ELISPOT is a method for detecting cytokine production at the single cell level whereas ELISA is a sensitive and specific method for quantification of different cytokines.

Antibody detection kits, such as the ExtrAvidin® Staining Kits (Sigma, St Louis, Mo.) are used to assay the presence of monoclonal antibody in nanoparticles. These kits comprise universal reagents for use with primary antibodies in immunohistology, ELISA, and immunoblotting. ExtrAvidin is a unique form of avidin that combines the high specificity and affinity of avidin for biotin with low non-specific binding at physiological pH. ExtrAvidin alkaline phosphatase and peroxidase enzymes thus exhibit high sensitivity with low background. For example, monoclonal anti-goat IgG antibodies in EXTRA-1 show no cross-reactivity with human IgG. Further, affinity isolated antibodies in EXTRA-2A and EXTRA-3A etc. have been adsorbed with human IgG and IgM to minimize cross-reactivity. Biotinylated antibodies contain a spacer which improves accessibility for the ExtrAvidin conjugates.

EXAMPLE NO. 19

Nanoparticles with Monoclonal Antibody

One aspect describes nanoparticles for oral administration in a patient comprising a positively charged shell substrate, a negatively charged core substrate, and a bioactive agent encapsulated within the nanoparticles, wherein the bioactive agent is monoclonal antibody. In one embodiment, the bioactive agent is mixed with, conjugated to, or coupled to the core substrate. In another embodiment, the bioactive agent is totally encapsulated within the nanoparticles.

Glycosaminoglycan (GAG), heparin, α-PGA, or γ-PGA is a negatively charged substrate that serves to bind with positively charged chitosan substrate to form a nanoparticle. Some aspects of the invention relate to GAG containing nanoparticles for oral administration. In one embodiment, GAG serves as at least a portion of the core substrate with chitosan serves as at least a portion of the shell substrate, wherein GAG conjugates at least one bioactive agent as disclosed herein, for example, monoclonal antibodies. In preparation, nanoparticles were obtained upon addition of aqueous solution (2 ml) of GAG and monoclonal antibody "Bevacizumab", using a pipette (0.5-5 ml, PLASTIBRAND®, BrandTech Scientific Inc., Germany), into a low-MW CS aqueous solution (pH 6.0, 10 ml) with excess CS concentrations under magnetic stirring at room temperature.

Nanoparticles were collected by ultracentrifugation at 38,000 rpm for 1 hour and coded mAb-NP, which is formed of shell substrate chitosan, core substrate GAG with encapsulated monoclonal antibody. The monoclonal antibody is wholly or substantially totally encapsulated in the nanoparticles. The nanoparticles have an average diameter from about 50 nm to about 500 nm. In a preferred embodiment, the nanoparticles are nanoshells having biodegradable chitosan as a shell substrate. The nanoparticles may further comprise a core substrate that mixes with the monoclonal antibody or monoclonal antibody anti-cancer drug. In clinical settings, the method of treating a tumor with a monoclonal antibody anti-cancer drug that is released from the nanoparticles comprises a step of binding the anti-cancer drug to a cell or tissue of the patient, wherein the binding is by the formation of an antigen-antibody complex or the formation of a ligand-receptor complex. In one embodiment, the cell or tissue is cancerous. As described above, the nanoparticles comprise a positively charged shell substrate and a negatively charged core substrate, wherein the nanoparticles have a surface charge from about +15 mV to about +50 mV.

Avastin is a recombinant humanized monoclonal IgG1 antibody that binds to and inhibits the biologic activity of human vascular endothelial growth factor (VEGF) in in vitro and in vivo assay systems, and is also sometimes described as a targeted therapy. Avastin is a particular type of targeted therapy called anti-angiogenic therapy that may interfere with the growth of new blood vessels, which provide nutrients to the tumor. Avastin is the first anti-angiogenic therapy in combination with first-line chemotherapy proven to help many people with metastatic colorectal cancer live longer. In clinical trials, patients taking Avastin in combination with chemotherapy experienced many benefits compared with those taking chemotherapy alone. In order to grow and spread, tumors need a constant supply of oxygen and other nutrients. Tumors get this supply by creating their own network of blood vessels. This process is called angiogenesis.

To start angiogenesis, a tumor sends out signals to nearby blood vessels. These signals cause new blood vessels to grow toward the tumor. Once these new vessels reach the tumor, they provide the supply of blood that provides oxygen and other nutrients to the tumor. Avastin is thought to work by interfering with the signals that cause angiogenesis. Avastin is given by infusion. Bevacizumab is produced in a Chinese Hamster Ovary mammalian cell expression system in a nutrient medium containing the antibiotic gentamicin and has a molecular weight of approximately 149 kilodaltons. AVASTIN is a clear to slightly opalescent, colorless to pale brown, sterile, pH 6.2 solution for intravenous (IV) infusion.

The obtained mAb-NP in Example no. 18 is broken up by extreme stirring/beating and the supernatant is assayed by ELISA to confirm the presence of Bevacizumab antibody in the sample with endothelial growth factor as target binding antigen.

Figure 19:
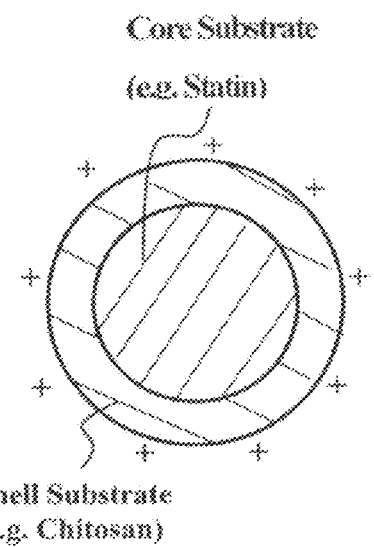
FIG. 19 shows a schematic composition of a nanoparticle with a shell substrate and a core substrate having a statin (HMG-COA reductase inhibitor).

Some aspects of the invention relate to a method of delivering a monoclonal antibody protein to a target tissue or a tumor of a patient, comprising the steps of: providing the monoclonal antibody protein to the target tissue or the tumor, wherein the monoclonal antibody protein is encapsulated within nanoparticles; administering the nanoparticles to the patient orally; and treating the target tissue or the tumor with the monoclonal antibody protein that is released from the nanoparticles. One preferred aspect of the invention relate to a method of treating a target tissue or organ of a patient with a monoclonal antibody, comprising the steps of: providing the monoclonal antibody to the tissue or organ, wherein the monoclonal antibody is encapsulated within nanoparticles; administering the nanoparticles to the patient orally; and treating the target tissue or organ with the monoclonal antibody that is sustained released from the nanoparticles. In one embodiment, the monoclonal antibody protein is an anti-cancer drug for the tumor. In another embodiment, the monoclonal antibody is Adalimumab for treating rheumatoid arthritis or psoriatic arthritis. In still another embodiment, the monoclonal antibody protein is Bevacizumab for treating tumor or cancer. FIG. 19 shows a schematic composition of a nanoparticle with a shell substrate and a core substrate having a monoclonal antibody. The method may further comprise a step of delivering the nanoparticles to the target tissue or tumor through intestinal absorption. In a preferred embodiment, the anti-cancer monoclonal antibody is directed against tumor vasculature. Some aspect provides that the target tumor is in an organ selected from the group consisting of breast, lung, brain, liver, skin, kidney, GI organ, prostate, bladder and gynecological organ.

EXAMPLE NO. 20

Nanoparticles with Monoclonal Antibody Adalimumab

Humira® (Adalimumab) is a recombinant human IgG1 monoclonal antibody specific for human tumor necrosis factor (TNF). It consists of 1330 amino acids and has a molecular weight of approximately 148 kilodaltons. The solution of Humira is clear and colorless, with a pH of about 5.2 and contains 40 mg Adalimumab in each 0.8 mL of single-use syringe. TNF is a naturally occurring cytokine that is involved in normal inflammatory and immune responses. Elevated levels of TNF are found in the synovial fluid of rheumatoid arthritis and psoriatic arthritis patients and play an important role in both the pathologic inflammation and the joint destruction that are hallmarks of these diseases.

Clinically, after treatment with Humira, a rapid decrease in levels of acute phase reactants of inflammation (C-reactive protein, erythrocyte sedimentation rate, and serum cytokines IL-6) was observed compared to baseline in patients with rheumatoid arthritis. Serum levels of matrix metalloproteinases (MMP-1 and MMP-3) that produce tissue remodeling responsible for cartilage destruction were also decreased after Humira administration. Humira is administered subcutaneously and/or intravenously. Adalimumab may also be effective against plaque psoriasis, ankylosing spondylitis or Crohn's disease. Crohn's disease is a chronic inflammatory disease of the intestines. The disease, once it starts tends to fluctuate between periods of inactivity (remission) and activity (relapse).

In preparation of nanoparticles encapsulating Adalimumab, the process comprises addition of aqueous solution (2 ml) of GAG and monoclonal antibody "Adalimumab" by using a pipette (0.5-5 ml, PLASTIBRAND®, BrandTech Scientific Inc., Germany), into a chitosan aqueous solution (pH 6.0, 10 ml) with excess CS concentrations under magnetic stirring at room temperature. Nanoparticles were collected by ultracentrifugation at 38,000 rpm for 1 hour and were assayed by ELISA technique to confirm the presence of Adalimumab monoclonal antibody in the nanoparticles with target binding antigen. One aspect of the invention describes a method of delivering a monoclonal antibody to a target tissue or organ of a patient, comprising the steps of: providing the monoclonal antibody to the tissue or organ, wherein the monoclonal antibody is encapsulated within nanoparticles; administering the nanoparticles to the patient orally; and treating the target tissue or organ with the monoclonal antibody that is controlled released from the nanoparticles. The method further comprises a step of delivering the nanoparticles to the target tissue or organ through intestinal absorption.

Complex of immunoglobulins with certain acidic polysaccharides was demonstrated in the literature (*Biochemistry* 1997;36:13187-13194) by the binding of the sulfated glycans agaropectin or heparin with certain human IgG proteins. The major binding force between heparin and the light chains of IgG is most likely electrostatic. This electrostatic interaction is between the cationic sites on certain IgG proteins and the anionic sulfate residues of agaropectin or heparin. Prior research describes that the interactions with multi-chain and single-chain rat skin heparin are stable under physiological conditions and involve the Fab and, more specifically, the Fv region of the IgG molecule (*J. Exp. Med.* 1981;153:883-896). The characteristics of heparin-IgG interaction resemble those of heparin with other plasma proteins, the interactions of which have biological significance. Available sulfated glycosaminoglycans include, but not limited to, chondroitin 6-sulfate, keratin sulfate, heparin, and dermatan sulfate. By ways of illustration, agaropectin found in agar preparations is a polysaccharide. Some of its galactosyl units are sulfated. Carrageenan has also sulfated side units for complexion.

The following ELISA method has been adopted or slightly modified for monoclonal antibody assay. The stock solutions include: PBS (20 mM NaPi pH=7.5, 150 mM NaCl), PT (0.1% Tween 20 in PBS), Blocking solution (3% BSA in PT; store at −20° C.), and Developing solution (10 mg o-phenylenediamine in 25 ml of a buffer with pH=5.5 plus 12 µl of 30% $H_2O_2$. This solution is light sensitive and is prepared just before use).

The ELISA procedures include:
1. Coat the plate wells with 50 µl of antigen (0.2 µg/ml in PBS). Incubate one hour at room temperature;
2. Wash the plate (discard the well solution, add 200 µl of PT per well and wait about 2 min. Repeat this cycle another 2 times and discard the late well solution);
3. Block the plate wells with 150 µl of blocking solution. Incubate one hour at room temperature;
4. Discard the blocking solution and add 50 µl of the hybridoma supernatants in different wells. Incubate 30 min at room temperature;
5. Wash the plate;
6. Add 50 µl of the peroxidase-coupled antimouseIgs antibody (1/5000 in blocking solution). Incubate 30 min at room temperature;
7. Wash the plate;
8. Incubate the plate wells with 100 µl of developing solution until color change is evident;
9. Stop the reaction by adding 50 µl of 2.5M $H_2SO_4$ per well; and
10. Measure the absorbance at 492 nm.

Adalimumab is an injectable protein that blocks the inflammatory effects of tumor necrosis factor alpha (TNF alpha) in rheumatoid arthritis. Two other injectable drugs—Infliximab (Remicade®) and etanercept (Enbrel®)—also block TNF alpha. One aspect of the invention provides a nanoparticle comprising a shell substrate of chitosan, a core substrate, and an encapsulated bioactive agent that blocks TNF-alpha, wherein the bioactive agent is selected from the group consisting of Adalimumab, Infliximab, etanercept, and the like. Adalimumab was constructed from a fully human monoclonal antibody, while infliximab is a mouse-human chimeric antibody and etanercept is a TNF receptor-IgG fusion protein. Inflammation is the body's reaction to injury and is a necessary process for the repair of injury. TNF is a protein that the body produces when there is inflammation. The TNF promotes inflammation and the signs of inflammation, which, in the case of arthritis, include fever as well as pain, tenderness, and swelling of joints. The unchecked inflammation of rheumatoid arthritis eventually leads to destruction of the joints. Adalimumab is a synthetic (man-made) protein, similar to human protein, that binds to TNF in the body and thereby blocks the effects of TNF. As a result, inflammation and fever as well as the pain, tenderness and swelling of joints are reduced in patients with rheumatoid arthritis. In addition, the progressive destruction of the joints is slowed or prevented. Adalimumab was approved by the FDA in December 2002.

Statin

The statins (or HMG-CoA reductase inhibitors) form a class of hypolipidemic agents, used as pharmaceuticals to lower cholesterol levels in people at risk for cardiovascular disease because of hypercholesterolemia. The first statin (Lovastatin) to be marketed in shown below.

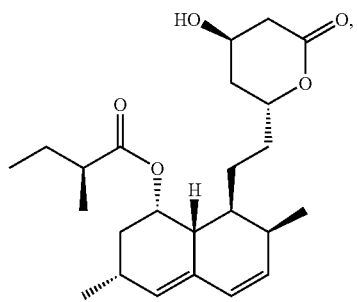

The statins include, in alphabetical order (brand names vary in different countries): Atorvastatin (Lipitor; disclosed in U.S. Pat. No. 4,681,893), Cerivastatin (Lipobay, Baycol; disclosed in U.S. Pat. No. 5,006,530), Fluvastatin (Lescol; disclosed in U.S. Pat. No. 4,739,073), Lovastatin (Mevacor, Altocor; disclosed in U.S. Pat. No. 4,231,938), Mevastatin (naturally-occurring compound, found in red yeast rice), Pravastatin (Pravachol, Selektine, Lipostat; disclosed in U.S. Pat. No. 4,346,227), Rosuvastatin (Crestor; disclosed in U.S. Pat. No. 5,260,440), Simvastatin (Zocor, Lipex; disclosed in U.S. Pat. No. 4,444,784), and Pitavastatin (disclosed in U.S. Pat. No. 5,011,930). Their chemical formulas are listed in U.S. Pat. No. 6,777,552 B2, entire contents of which are incorporated herein by reference. LDL-lowering potency varies between agents. Among the above-identified statins, pravastatin, fluvastatin, cerivastatin, atovastatin, rosuvastatin, and pitavastatin are in acidic forms (that is, having carboxylic units) and can become sodium or calcium salt forms. One aspect of the invention relates to a nanoparticle comprising positively charged shell substrate chitosan and negatively charged core substrate statins, such as the ones with carboxylic units. In one embodiment, the statins are complexed with chitosan, low MW chitosan, or chitosan derivatives.

Statins act by competitively inhibiting HMG-CoA reductase, an enzyme of the HMG-CoA reductase pathway, the body's metabolic pathway for the synthesis of cholesterol. Although statins inhibit endogenous cholesterol synthesis, their action goes further than that. By reducing intracellular cholesterol levels, they cause liver cells to upregulate expression of the LDL receptor, leading to increased clearance of low-density lipoprotein from the bloodstream. Due to its sustained release characteristics of the nanoparticle system of the present invention (as evidenced in FIG. 15), one aspect provides a nanoparticle that encapsulates at least one statin adapted for sustained release and sustained inhibition of the HMG-CoA reductase pathway (Berg, J. M., J. L. Tymoczko, and L. Stryer, Biochemistry. 5th ed. 2002, New York: W.H. Freeman. xxxviii, 974). Statins is one drug that targets the HMG-CoA reductase pathway (used for elevated cholesterol levels). Another bioactive agent for targeting the HMG-CoA reductase pathways is Bisphosphonates (used for osteoporosis).

Statins exhibit action beyond lipid-lowering activity in the prevention of atherosclerosis. Researchers believe that statins prevent cardiovascular disease via four proposed mechanisms: improving endothelial function, modulating inflammatory responses, maintaining plaque stability, and preventing thrombus formation. It was recently reported that statin therapy could significantly reduce morbidity and mortality in diabetics. The decision to treat is based on vascular risk and not initial cholesterol levels (MRC/BHF Heart Protection Study of cholesterol-lowering with simvastatin in 5963 people with diabetes: a randomized placebo-controlled trial. Lancet 2003 361: 2005-2016). Therefore, it is contemplated that insulin and statin may be co-encapsulated in nanoparticles system of the present invention.

Very high-intensity statin therapy can result in significant regression of coronary atherosclerosis. A landmark two-year study demonstrated that CRESTOR™ (rosuvastatin) reversed plaque build-up in the arteries of patients with evidence of coronary artery disease. Researchers at the Cleveland Clinic treated 507 patients with 40 mg/d for 24 months and use intravascular ultrasound before and after treatment to measure changes in atheroma volume. This is the first time a statin has demonstrated regression of atherosclerosis in a major clinical study. Data presented from ASTEROID, at the 55th Annual Scientific Session of the American College of Cardiology (ACC) in 2006 and published in the April $5^{th}$ issue of the Journal of the American Medical Association show that plaque build-up in patients' arteries was reduced by between seven and nine per cent. These significant changes were achieved with CRESTOR and were associated with significant reductions in LDL-C or 'bad' cholesterol (53 per cent, $p<0.001$) and increases in HDL-C or 'good' cholesterol (15 per cent, $p<0.001$).

With evidence from observational studies, as well as retrospective analyses of previous trials, there had been speculation that statins might play a role in reducing the recurrence of ventricular arrhythmias. New results from a prospective, randomized, placebo-controlled clinical trial support that hypothesis, with the evidence suggesting that statins appear to have antiarrhythmic effects (De Sutter J et al. "Intensive lipid-lowering therapy and ventricular arrhythmias in patients with coronary artery disease and internal cardioverter defibrillators" Heart Rhythm Society 2006 Scientific Sessions; May 17-20, 2006; Boston, Mass.). Intensive lipid-lowering therapy, using atorvastatin 80 mg, is an effective and safe way to reduce the recurrence of ventricular arrhythmias in patients with coronary artery disease and ICD implants. It was reported that treatment with atorvastatin resulted in a statistically significant 59% reduction in the number of days with an appropriate ICD intervention and high-dose statin therapy in these patients was safe and well tolerated, with no statistically significant treatment-related adverse events observed.

Statins do not increase the risk for breast cancer and hydrophobic statins may decrease the risk, according to the results of an analysis of the Women's Health Initiative (WHI) study (J Natl Cancer Inst. 2006;98:700-707). To evaluate associations between type of statin used, potency, duration of use, and risk for invasive breast cancer, the investigators examined data for 156,351 postmenopausal women enrolled in the WHI, of whom 11,710 (7.5%) used statins. During an average follow-up of 6.7 years, 4383 invasive breast cancers were identified by review of medical records and pathology reports. Breast cancer incidence was 4.09 per 1000 person-years for statin users and 4.28 per 1000 person-years for nonusers. Duration of statin use did not affect risk. Hydrophobic statins, such as simvastatin, lovastatin, and fluvastatin, were used by 8106 women, and their use was associated with an 18% lower incidence of breast cancer. Use of other statins, such as pravastatin and atorvastatin, or nonstatin lipid-lowering agents, was not associated with breast cancer incidence. A number of different mechanisms have been identified by which hydrophobic statins might inhibit the growth of cancer. In this large population of postmenopausal women with well-characterized breast cancer risk factors, when all statins were considered together as a class, no statistically significant association with breast cancer incidence was seen.

EXAMPLE NO. 21

Nanoparticles with Encapsulated Statin

FIG. 19 shows a schematic composition of a nanoparticle with a shell substrate and a core substrate having a statin (HMG-CoA reductase inhibitor). In product formulation, nanoparticles were obtained upon addition of statin (in one example for illustration, atorvastatin) aqueous solution (2 ml), using a pipette (0.5-5 ml, PLASTIBRAND®, BrandTech Scientific Inc., Germany), into a low-MW CS aqueous solution (pH 6.0, 10 ml) with excess CS concentrations under magnetic stirring at room temperature. Nanoparticles were collected by ultracentrifugation at 30,000 rpm for 1 hour. Nanoparticles comprise positively charged shell substrate chitosan and negatively charged core substrate statins. Statin is totally or substantially totally encapsulated in the nanoparticles. In other words, statin component is substantially maintained within the intact nanoparticles during the nanoparticle delivery phase orally. Thus, statin does not cause any significant effect until the nanoparticles dissociate or biodegrade to release the core contents in a sustained release manner.

Some aspects of the invention relate to a method of delivering an HMG-CoA reductase inhibitor to blood circulation in a patient, comprising: (a) providing nanoparticles that encapsulate the HMG-CoA reductase inhibitor, wherein the nanoparticles are biodegradable; (b) administering the nanoparticles orally toward an intestine of the patient; (c) urging the nanoparticles to pass through an epithelial barrier of the intestine; and (d) releasing the HMG-CoA reductase inhibitor into the blood circulation in a sustained manner. The sustained release of a bioactive agent from a chitosan-shelled nanoparticle has been demonstrated in FIG. 15, with reference to that via subcutaneous injection. In one aspect of the invention, the method further comprises a step of enhancing the chitosan-shelled nanoparticles to adhere to a mucosal surface of the intestine for paracellular transport. In one embodiment, the HMG-CoA reductase inhibitor is a statin or bisphosphonates.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A pharmaceutical composition of nanoparticles for oral administration in a patient, said nanoparticles comprising a shell portion of biodegradable chitosan that is positively charged, a core portion that consists of positively charged chitosan and one negatively charged substrate, wherein said negatively charged substrate is neutralized with a portion of said positively charged chitosan in the core portion, and a HMG-CoA reductase inhibitor loaded within said nanoparticles.

2. The pharmaceutical composition of claim 1, wherein said negatively charged substrate in the core portion is poly (glutamic) acid (PGA).

3. The pharmaceutical composition of claim 2, wherein said PGA is γ-PGA, α-PGA, derivatives or salts of PGA.

4. The pharmaceutical composition of claim 1, wherein said negatively charged substrate in the core portion is heparin or glycosaminoglycan.

5. The pharmaceutical composition of claim 1, wherein a surface of said nanoparticles is characterized with a positive surface charge.

6. The pharmaceutical composition of claim 1, wherein said nanoparticles have a surface charge from about +15 mV to about +50 mV.

7. The pharmaceutical composition of claim 1, wherein said nanoparticles are loaded in a capsule or tablet.

8. The pharmaceutical composition of claim 7, wherein said capsule or tablet is treated with an enteric coating.

9. The pharmaceutical composition of claim 1, wherein said HMG-CoA reductase inhibitor is a statin.

10. The pharmaceutical composition of claim 1, wherein said HMG-CoA reductase inhibitor is a statin selected from the group consisting of lovastatin, simvastatin, pravastatin, fluvastatin, cerivastatin, atovastatin, rosuvastatin, pitavastatin, and combinations thereof.

11. The pharmaceutical composition of claim 1, wherein said HMG-CoA reductase inhibitor is bisphosphonates.

12. The pharmaceutical composition of claim 1, wherein said nanoparticles are formed via a simple and mild ionic-gelation method.

13. A method of delivering an HMG-CoA reductase inhibitor to blood circulation in a patient, comprising:
    providing nanoparticles according to the pharmaceutical composition of claim 1;
    administering said nanoparticles orally toward an intestine of the patient;
    passing said nanoparticles through an epithelial barrier of the intestine; and
    releasing said HMG-CoA reductase inhibitor into the blood circulation.

14. The pharmaceutical composition of claim 7, wherein at least one absorption enhancer is co-encapsulated with said nanoparticles in the capsule.

15. The pharmaceutical composition of claim 7, wherein the capsule further comprises a second nanoparticle that contains at least one absorption enhancer.

16. The pharmaceutical composition of claim 9, wherein the statin is somatostatin or synthetic analogues, modifications and pharmacologically active fragments thereof.

* * * * *